United States Patent [19]

Entschel et al.

[11] 4,213,898
[45] Jul. 22, 1980

[54] CATIONIC 5-ARYLAZO-6-HYDROXYPYRIDONE-2 DYES

[75] Inventors: Roland Entschel, Basel; Curt Mueller, Binningen; Willy Steinemann, Basel, all of Switzerland

[73] Assignee: Sandoz Ltd., Basel, Switzerland

[21] Appl. No.: 400,527

[22] Filed: Sep. 25, 1973

Related U.S. Application Data

[63] Continuation-in-part of Ser. No. 824,298, May 13, 1969, abandoned.

[30] Foreign Application Priority Data

May 15, 1968 [CH] Switzerland .................. 7218/68
Aug. 2, 1968 [CH] Switzerland .................. 11581/68
Aug. 13, 1968 [CH] Switzerland .................. 12136/68

[51] Int. Cl.² .............. C09B 29/36; C09B 31/14; D06P 1/08; D06P 3/70
[52] U.S. Cl. .................. 260/156; 260/37 R; 260/39 P; 260/40 R; 260/42.21; 260/146 D; 260/146 R; 260/154; 260/155
[58] Field of Search .............. 260/156, 146 R, 155, 260/154, 153

[56] References Cited

U.S. PATENT DOCUMENTS

| | | | |
|---|---|---|---|
| 2,099,525 | 11/1937 | Krzikalla et al. | 260/156 X |
| 2,234,723 | 3/1941 | Pickey et al. | 260/156 |
| 2,431,190 | 11/1947 | Morgan | 260/156 X |
| 3,252,964 | 5/1966 | Fuchs et al. | 260/152 |
| 3,402,167 | 9/1968 | Entschel | 260/154 |
| 3,487,060 | 12/1969 | Ritter et al. | 260/156 |
| 3,518,247 | 6/1970 | Altermatt et al. | 260/156 |
| 3,577,404 | 5/1971 | Entschel et al. | 260/162 |
| 3,642,769 | 2/1972 | Moritz et al. | 260/156 X |
| 3,658,781 | 4/1972 | Hegar | 260/156 |

Primary Examiner—Floyd D. Higel

Attorney, Agent, or Firm—Gerald D. Sharkin; Richard E. Vila; Melvyn M. Kassenoff

[57] ABSTRACT

Azo dyes of the formula

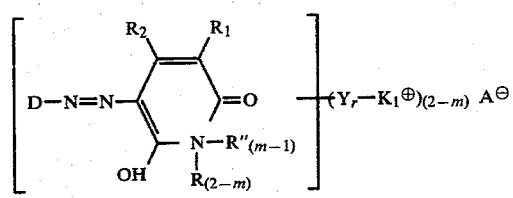

wherein
D is an aromatic carbocyclic or heterocyclic diazo component radical,
R is hydrogen or optionally substituted hydrocarbyl, heterocyclyl or amino,
R″ is quaternized nitrogen-containing heterocyclyl,
$R_1$ is hydrogen or cyano,
$R_2$ is optionally substituted alkyl, aryl or heterocyclyl,
Y is a divalent bridge member,
$K_1^\oplus$ is optionally substituted ammonium, hydrazinium or quaternized nitrogen-containing heterocyclyl,
m is 1 or 2,
r is 0 or 1, and
$A^\ominus$ is an anion.

The $Y_r$-$K_1^\oplus$ group is preferably attached to the nitrogen atom of the pyridone ring or to the diazo component radical D. These dyes are well-suited for dyeing and printing textiles which consist of or contain fibers of polyacrylonitrile or acrylonitrile copolymers as well as polyamides and polyesters that have been modified to contain acid groups. The obtained dyeings are level and exhibit good fastness to light and wet treatments as well as organic solvents and are stable to boiling and pH conditions.

27 Claims, No Drawings

CATIONIC 5-ARYLAZO-6-HYDROXYPYRIDONE-2 DYES

This application is a continuation-in-part of application Ser. No. 824,298, filed on May 13, 1969, and now abandoned.

This application is directed to basic azo dyes having a 6-hydroxypyridone-2 coupling component which are useful for dyeing and printing textiles which consist of or contain fibers of polyacrylonitrile or acrylonitrile copolymers.

The dyes of this application have the formula

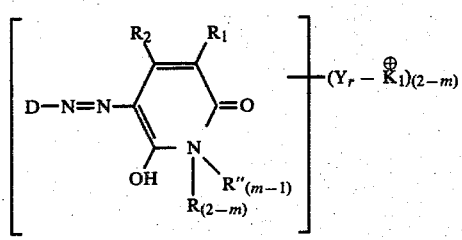

wherein

D is carbocyclic aryl or heterocyclic aryl which may be substituted, $R_1$ is hydrogen or cyano, $R_2$ is alkyl, aryl or heterocyclyl which may be substituted, R is hydrogen, hydrocarbyl which may be substituted, heterocyclyl or amino which may be substituted (e.g., by substituents capable of adding on a proton),

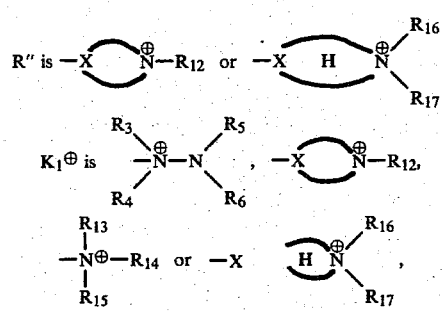

Y is a divalent bridge member, each of $R_3$ and $R_4$ is independently alkyl or cycloalkyl which may be substituted, or $R_3$ and $R_4$ taken together and with the nitrogen to which they are joined are heterocyclyl, each of $R_5$ and $R_6$ is independently hydrogen or alkyl or cycloalkyl which may be substituted, or $R_3$ together with $R_5$ and/or $R_4$ together with $R_6$ and the nitrogen atoms to which they are joined are heterocyclyl, $R_{12}$ is hydrocarbyl which may be substituted, each of $R_{13}$, $R_{14}$ and $R_{16}$ is independently hydrocarbyl which may be substituted, $R_{15}$ is alkyl or cycloalkyl which may be substituted, or $R_{13}$ and $R_{14}$ or $R_{13}$, $R_{14}$ and $R_{15}$ taken together and with the nitrogen atom to which they are joined are heterocyclyl, $R_{17}$ is hydrocarbyl, substituted hydrocarbyl, amino or substituted amino, X is a carbon or nitrogen atom,

is the radical of a multimembered (e.g., five- or six-membered) saturated or partially saturated ring which may be further substituted,

is the radical of an unsaturated ring (e.g., a five- or six-membered ring) which may be substituted, $A^\ominus$ is an anion, m is 1 or 2, and r is 0 or 1.

Dyes of the formula

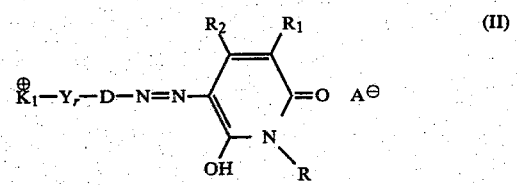

and particularly those of the formula

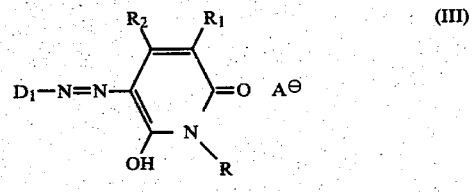

wherein $D_1$ is

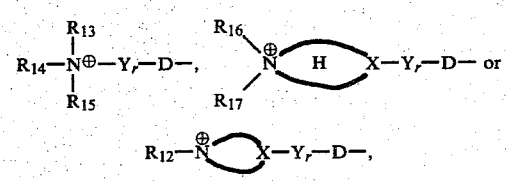

are of good quality.

Dyes of the formulae

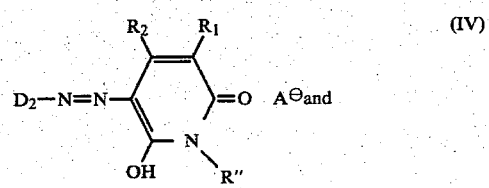

-continued

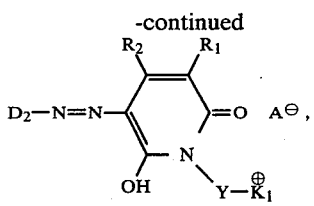 (V)

wherein D₂ is carbocyclic aryl or heterocyclic aryl which may be substituted,
with the proviso that D₂ is free of cationic groups, are of equally good quality.

Particularly good dyes are those of Formulae I, II, III, IV and V
wherein $R_1$ is cyano as well as those dyes
wherein $R_2$ is alkyl or phenyl, and particularly those dyes
wherein $R_1$ is cyano, and
$R_2$ is alkyl or phenyl.

Each term and variable that appears in the specification and/or claims has, unless it is otherwise defined, the meaning previously given to said term or variable. If any term or variable is not defined prior to its appearance, it has the definition subsequently given to it.

Halo is preferably chloro, bromo or fluoro.

Examples of hydrocarbyl radicals are optionally substituted alkyl and cycloalkyl radicals and optionally substituted aryl radicals, e.g., cyclohexyl, alkylcyclohexyl and phenyl radicals.

Alkyl radicals are straight or branched and generally contain 1 to 12 or 1 to 6 carbon atoms and preferably 1, 2, 3 or 4 carbon atoms. The preferred substituents of the substituted alkyl groups are halo, hydroxy, cyano, aryl (e.g., phenyl) and protonizable amino groups. Where the substituent of substituted alkyl is aryl, substituted alkyl is aralkyl, e.g., benzyl. Cycloalkyl radicals may contain up to 12 or 6 carbon atoms and preferably contain 6 carbon atoms. When substituted, they contain the aforementioned substituents as well as alkyl groups.

Alkoxy radicals generally contain 1 to 6 carbon atoms, preferably 1, 2 or 3 carbon atoms.

All of the aryl radicals (including the carbocyclic aryl and heterocyclic aryl radicals, e.g., phenyl, naphthyl, tetrahydronaphthyl, pyridyl, quinolyl and tetrahydroquinolyl radicals) may be substituted, particularly by non-water solubilizing substituents, e.g., halo, nitro, cyano, thiocyano, hydroxy, alkyl, alkoxy, trifluoroalkyl, trichloroalkyl, phenyl, phenoxy, amino, alkylamino, dialkylamino, anilino, acyl, acyloxy, acylamino (e.g., urethane, alkylsulfonyl, arylsulfonyl, sulfamoyl, alkylsulfamoyl, dialkylsulfamoyl and arylsulfamoyl) and arylazo (e.g., phenylazo, diphenylazo and naphthylazo).

The protonizable groups are groups that contain a nitrogen atom which, in acid medium, and particularly in a mineral acid medium, add on a proton, i.e., which form salts with the addition of a proton. In this context, protonizability is the capacity of a nitrogen atom to add a proton, e.g., that of a mineral acid such as hydrochloric acid, so as to render the dye water-soluble.

The heterocyclic radicals and the groups of the formulae

-continued

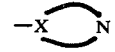

are, for example, radicals of saturated, partially saturated or unsaturated, optionally substituted multimembered rings, preferably 5- or 6-membered rings, on which further cycloaliphatic, heterocyclic or aromatic rings may be condensed, e.g., pyridine, quinoline, piperidine, pyrrolidine, morpholine, aziridine, piperazine, isoquinoline, tetrahydroquinoline, pyrazole, triazole, pyridazine, imidazole, pyrimidine, thiazole, benzothiazole, thiadiazole, indazole, pyrrole, indole, oxazole, isoxazole, pyrazoline, tetrazole and thiophene rings.

Examples of heterocyclic rings formed by $R_3$ and $R_4$ taken together and with the nitrogen to which they are joined are pyrrolidine, piperazine, morpholine, aziridine and piperidine rings.

The heterocyclic rings formed by $R_3$ together with $R_5$ and/or $R_4$ together with $R_6$ and the nitrogen atoms to which they are joined are saturated or unsaturated rings, preferably containing 5 or 6 members, e.g., pyrazolidine, pyridazine and pyrazoline rings (including trimethylenepyrazolidine and tetramethylpyrazoline).

Examples of heterocyclic rings formed by $R_{13}$ and $R_{14}$ taken together and with the nitrogen to which they are joined are pyrrolidine, piperidine, morpholine, aziridine and piperazine rings.

Examples of heterocyclic rings formed by $R_{13}$, $R_{14}$ and $R_{15}$ taken together and with the nitrogen to which they are joined are pyridine rings (including quinoline rings) and the group of the formula

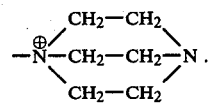

Examples of R and R'' are radicals of the formulae

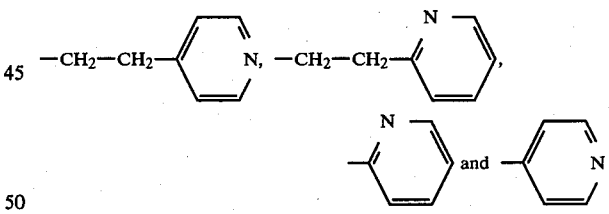

wherein the nitrogen atom may be quaternized.

The optionally substituted amino group may be a primary, secondary or tertiary amino group or, in a suitable case, a quaternary ammonium group. Examples of substituents on the amino group are alkyl, arylalkyl, cycloalkyl and aryl radicals (e.g., phenyl radicals).

The divalent bridge members Y may be, for example, substituted alkylene radicals or alkylene radicals having 1 to 12 or preferably 1 to 6 carbon atoms. These radicals may be straight or branched and may be attached to ring members or interrupted by ring members, e.g., cyclohexylene and phenylene radicals, or hetero atoms or groups of hetero atoms, e.g.,

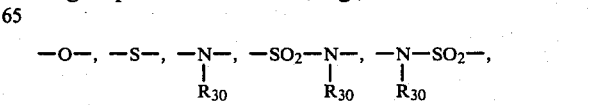

-continued

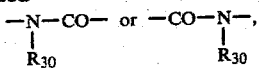

wherein R₃₀ is hydrogen or an optionally substituted hydrocarbyl radical.

The divalent bridge members Y are preferably bound through a carbon atom to the K⊕ (e.g., K₁⊕) groups. The K⊕ groups are bound to the right-hand end of the Y groups as written in the specification and claims.

Examples of divalent bridge members are —CO—, —SO₂—, —(CH₂)$_p$—,

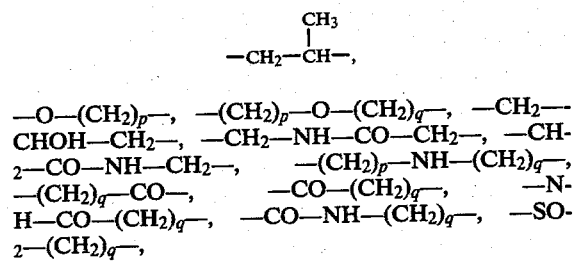

—O—(CH₂)$_p$—, —(CH₂)$_p$—O—(CH₂)$_q$—, —CH₂—CHOH—CH₂—, —CH₂—NH—CO—CH₂—, —CH₂—CO—NH—CH₂—, —(CH₂)$_p$—NH—(CH₂)$_q$—, —(CH₂)$_q$—CO—, —CO—(CH₂)$_q$—, —NH—CO—(CH₂)$_q$—, —CO—NH—(CH₂)$_q$—, —SO₂—(CH₂)$_q$—,

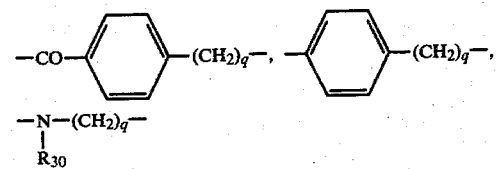

and —NH—CH₂—CHOH—CH₂—, wherein each of p and q is independently 1 to 6.

The anion A⊖ may be organic or inorganic. Examples of A⊖ are halide, e.g., chloride, bromide and iodide, sulfate, disulfate, methylsulfate, aminosulfonate, perchlorate, carbonate, bicarbonate, phosphate, phosphorus molybdate, phosphotungstate, phosphotungstic molybdate, benzenesulfonate, 4-chlorobenzenesulfonate, naphthalenesulfonate, oxalate, maleinate, acetate, propionate, lactate, succinate, chloroacetate tartrate, methanesulfonate, benzoate and complex anions, e.g., that of zinc chloride double salts.

More particularly, the compounds of this application have the formula

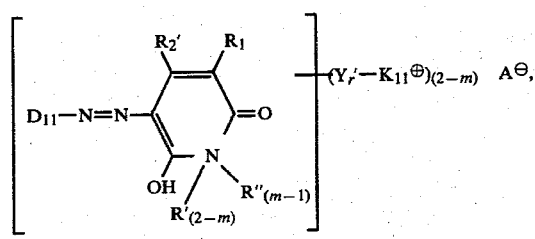

wherein
D₁₁ is phenyl, naphthyl, tetrahydronaphthyl, pyridyl, quinolyl, tetrahydroquinolyl, 1,2,4-triazolonyl, 1,2,4-triazolyl, indazolyl, 1,3,4-thiadiazolyl, thiazolyl or benzothiazolyl, or a substituted derivative thereof, wherein each substituent is independently halo, nitro, cyano, thiocyano, hydroxy, alkyl, alkoxy, trifluoroalkyl, trichloroalkyl, phenyl, phenoxy, chlorophenoxy, amino, alkylamino, dialkylamino, anilino, 2,4-dinitroanilino, acyl, acyloxy, acylamino (e.g., carbamyl, phenylcarbamoyl, alkylsulfonyl, arylsulfonyl, sulfamoyl, alkylsulfamoyl, dialkylsulfamoyl, arylsulfamoyl, N-alkyl-N-phenylsulfamoyl, alkylcarbonyl, alkoxycarbonyl, alkylcarbonylamino, benzamido, benzoyl and alkylbenzoyl), phenylazo, diphenylazo or naphthylazo, R₁ is hydrogen or cyano, R₂' is alkyl, carbocyclic aryl, benzyl or heterocyclyl, R' is hydrogen, alkyl, substituted alkyl, alkoxyalkyl, cyclohexyl, carbocyclic aryl, substituted carbocyclic aryl, heterocyclyl, substituted heterocyclyl, amino or substituted amino, R'' is

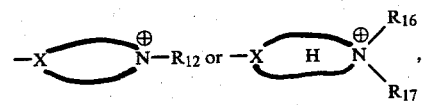

Y' is —Alk—, —Z—Alk—, —Alk—Z—, —Alk'—Z—Alk'—, —CO—, —SO₂— or

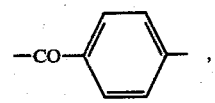

wherein Alk is straight or branched chain alkylene of 1 to 12 carbon atoms or straight or branched chain alkylene of 1 to 12 carbon atoms substituted by halo, hydroxy, cyano, phenyl, dialkylamino or piperidino, (preferably unsubstituted or substituted by hydroxy), each Alk' is independently straight or branched chain alkylene or straight or branched chain alkylene substituted by halo, hydroxy, cyano, phenyl, dialkylamino or piperidino (preferably unsubstituted), with the proviso that the two Alk' radicals together contain 2 to 12 carbon atoms, and

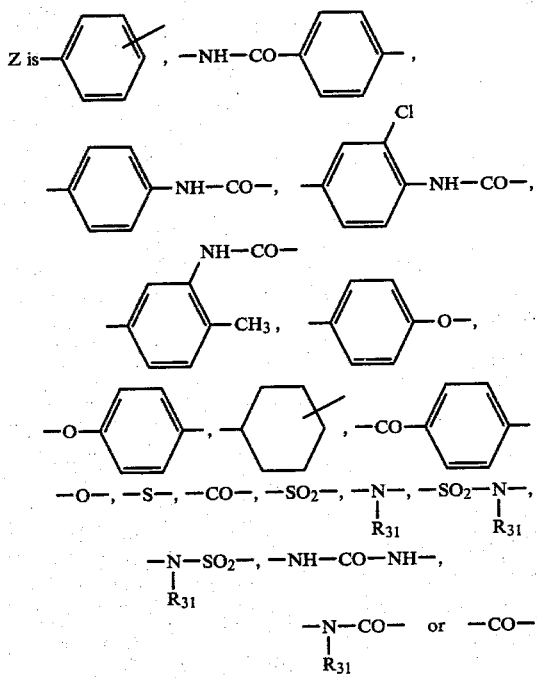

wherein $R_{31}$ is hydrogen, alkyl, substituted alkyl, cyclohexyl, alkylcyclohexyl, carbocyclic aryl or substituted carbocyclic aryl, wherein each substituent of substituted alkyl is independently halo, hydroxy, cyano or phenyl, each carbocyclic aryl is independently phenyl, naphthyl, or tetrahydronaphthyl and each substituent of substituted carbocyclic aryl is independently halo, nitro, cyano, thiocyano, hydroxy, alkoxy, alkyl, trifluoroalkyl, trichloroalkyl, phenyl, phenoxy, amino, alkylamino, dialkylamino, anilino, acyl, acyloxy, acylamino (e.g., carbamyl groups, alkylsulfonyl, arylsulfonyl, sulfamoyl, alkylsulfamoyl, dialkylsulfamoyl and arylsulfamoyl), phenylazo, diphenylazo or naphthylazo ($R_{31}$ is preferably hydrogen or alkyl (e.g., methyl)), $K_{11}^{\oplus}$ is 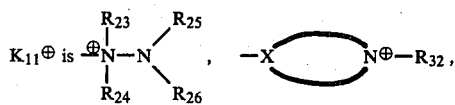

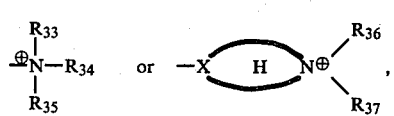

m is 1 or 2,
r is 0 or 1, and
$A^{\ominus}$ is an anion,
wherein
each of $R_{23}$ and $R_{24}$ is independently alkyl, substituted alkyl, cycloalkyl or substituted cycloalkyl, or $R_{23}$ and $R_{24}$ taken together and with the nitrogen to which they are joined form a pyrrolidinium, piperazinium, morpholinium, aziridinium or piperidinium ring, each of $R_{25}$ and $R_{26}$ is independently hydrogen, alkyl, substituted alkyl, cycloalkyl or substituted cycloalkyl, each of $R_{32}$, $R_{33}$, $R_{34}$ and $R_{36}$ is independently alkyl, substituted alkyl, carbocyclic aryl or substituted carbocyclic aryl, $R_{35}$ is alkyl, substituted alkyl, cycloalkyl or substituted cycloalkyl, and $R_{37}$ is amino, substituted amino, alkyl, substituted alkyl, cycloalkyl, substituted cycloalkyl, carbocyclic aryl or substituted carbocyclic aryl, or $R_{23}$ and $R_{25}$ taken together and with the nitrogens to which they are joined form a pyrazolidinium, pyridazinium or pyrazolinium ring, or $R_{23}$, $R_{24}$, $R_{25}$ and $R_{26}$ taken together with with the nitrogens to which they are joined form a

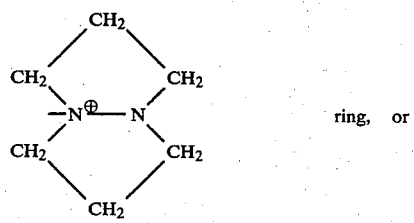 ring, or $R_{33}$ and $R_{34}$ taken together and with the nitrogen to which they are joined form a pyrrolidinium, piperidinium, morpholinium, aziridinium or piperazinium ring, or $R_{33}$, $R_{34}$ and $R_{35}$ taken together and with the nitrogen to which they are joined are

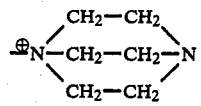

or a pyridinium or quinolinium ring,

is a piperidinium, pyrrolidinium, morpholinium, aziridinium, piperazinium or pyrazolinium ring, and $$-X\underset{\phantom{H}}{\overset{\oplus}{N}}-$$

is a pyridinium, quinolinium, isoquinolinium, tetrahydroquinolinium, pyrazolium, triazolium, pyridazinium, imidazolium, pyrimidinium, thiazolium, benzothiazolium, thiadiazolium, indazolium, pyrrolium, indolium, oxazolium, isoxazolium or tetrazolium ring,
wherein
each substituent of substituted alkyl is independently halo, hydroxy, cyano or phenyl, each substituent of substituted cycloalkyl is independently halo, hydroxy, cyano, phenyl or alkyl, each substituent of substituted carbocyclic aryl and substituted heterocyclyl is independently halo, nitro, cyano, thiacyano, hydroxy, alkyl, alkoxy, trifluoroalkyl, trichloroalkyl, phenyl, phenoxy, amino, alkylamino, dialkylamino, anilino, alkylsulfonyl, carbocyclic arylsulfonyl, sulfamoyl, alkylsulfamoyl, dialkylsulfamoyl, carbocyclic arylsulfamoyl, phenylazo, diphenylazo or naphthylazo, each substituent of substituted amino is independently alkyl, cycloalkyl, carbocyclic aryl or carbocyclic arylalkyl, each carbocyclic aryl is independently phenyl, naphthyl or tetrahydronaphthyl, each heterocyclyl is independently a pyridyl, quinolyl, tetrahydroquinolyl, piperidyl, pyrrolidinyl, morpholinyl, aziridinyl, piperazinyl, isoquinolyl, pyrazolinyl, triazolyl, triazolonyl, pyridazinyl, imidazolyl, pyrimidinyl, thiazolyl, benzothiazolyl, indazolyl, pyrrolyl, indolyl, oxazolyl, isoxazolyl, pyrazolinyl, trimethylenepyrazolidinyl, thienyl or tetrazolyl ring, each alkyl, cycloalkyl, alkyl radical of each alkoxyalkyl, trifluoroalkyl, trichloroalkyl, alkylamino, dialkylamino, alkylcarbonyl, alkylbenzoyl, alkylcarbonylamino, alkylsulfonyl, alkylsulfamoyl, dialkylsulfamoyl, N-alkyl-N-phenylsulfamoyl, alkyl chain of substituted alkyl and cycloalkyl ring of substituted cycloalkyl independently has not more than 12 carbon atoms, and each alkoxy and alkoxy radical of alkoxycarbonyl and alkoxyalkyl independently has 1 to 6 carbon atoms.

Preferred are the compounds of the formula

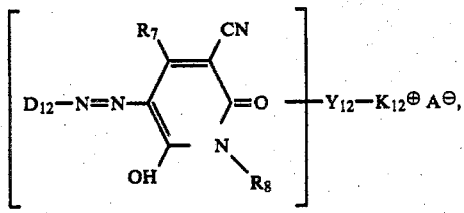

(VII)

wherein

D$_{12}$ is phenyl, substituted phenyl having 1 to 3 substituents or naphthyl, wherein each substituted of substituted phenyl is independently chloro, bromo, nitro, cyano, alkyl, alkoxy, phenyl, phenoxy, 4-chlorophenoxy, 2,4-dinitroanilino, alkylcarbonyl, benzoyl, alkylbenzoyl, alkoxycarbonyl, phenylcarbamoyl, alkylcarbonylamino, benzamido, sulfamoyl, alkylsulfamoyl, dialkylsulfamoyl, N-alkyl-N-phenylsulfamoyl, phenylsulfamoyl or phenylazo, R$_7$ is alkyl, benzyl or phenyl, R$_8$ is hydrogen or alkyl, Y$_{12}$ is

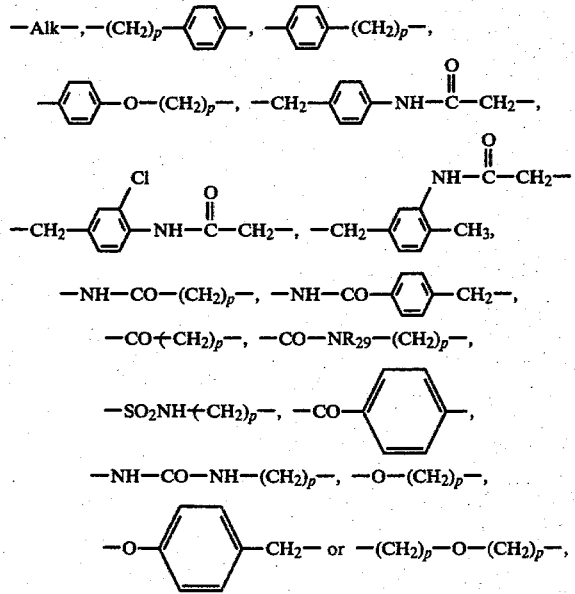

wherein Alk is straight or branched chain alkylene of 1 to 6 carbon atoms, each p is independently 1 to 6 and R$_{29}$ is hydrogen or alkyl,

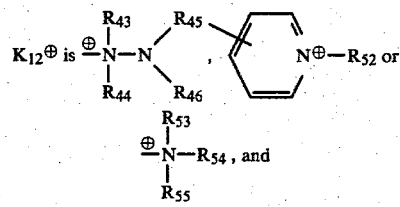

A$^\ominus$ is an anion, wherein each of R$_{43}$ and R$_{44}$ is alkyl, 2-hydroxyethyl or 2-cyanoethyl, or R$_{43}$ and R$_{44}$ taken together and with the nitrogen to which they are joined are pyrrolidinium, piperidinium or morpholinium, each of R$_{45}$ and R$_{46}$ is independently hydrogen or alkyl, each of R$_{52}$, R$_{53}$ and R$_{54}$ is independently alkyl, R$_{55}$ is alkyl or benzyl, or R$_{53}$ and R$_{54}$ taken together and with the nitrogen to which they are joined are pyrrolidinium, piperidinium or morpholinium, or R$_{53}$, R$_{54}$ and R$_{55}$ taken together and with the nitrogen to which they are joined are pyridinium, methylpyridinium or quinolinium, each alkyl and alkyl group of each alkylcarbonyl, alkylbenzoyl, alkylcarbonylamino, alkylsulfamoyl, dialkylsulfamoyl and N-alkyl-N-phenylsulfamoyl independently has 1 to 4 carbon atoms, and each alkoxy and alkoxy group of each alkoxycarbonyl independently has 1 to 3 carbon atoms.

Of special interest are the compounds of Formula VI having the formula

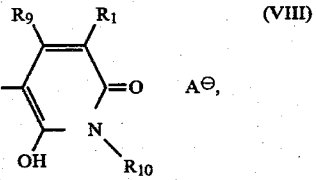

(VIII)

wherein

D$_{13}$ is phenylene or substituted phenylene, wherein each substituent of substituted phenylene is independently chloro, bromo, nitro, methyl, ethyl, methoxy, ethoxy or phenoxy (preferably phenylene or substituted phenylene having 1 or 2 substituents), R$_1$ is hydrogen or cyano (preferably cyano), R$_9$ is alkyl or phenyl (preferably methyl), R$_{10}$ is hydrogen, alkyl, monosubstituted alkyl, cyclohexyl or phenyl, wherein the substituent of monosubstituted alkyl is alkoxy, hydroxy or phenyl (when R$_{10}$ is alkoxyalkyl it is preferably methoxyalkyl), Y$_{13}$ is

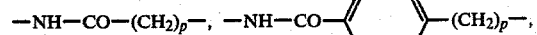
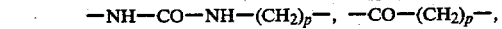
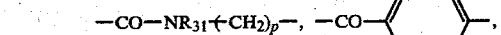

wherein p is 1 to 6, (preferably —NH—CO—CH$_2$—,

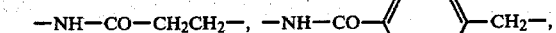
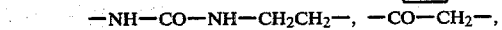
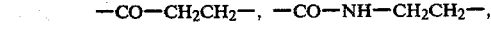

-continued

—CO—NH—CH₂CH₂CH₂—, —CO—N(CH₃)—CH₂CH₂—,

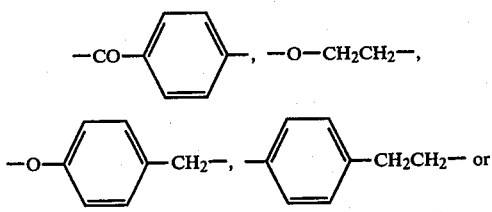

—SO₂—NH—CH₂CH₂—), K₁₃⊕ is

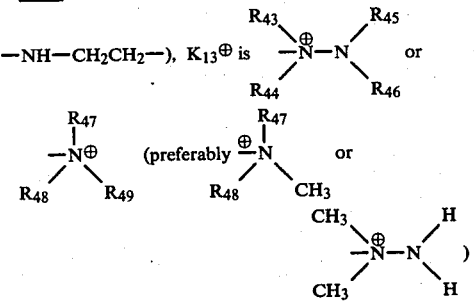

each of R₄₃ and R₄₄ is independently alkyl (preferably methyl), each of R₄₅ and R₄₆ is independently hydrogen or alkyl (preferably hydrogen), each of R₄₇ and R₄₈ is independently alkyl or hydroxyalkyl, and R₄₉ is alkyl (preferably methyl), or R₄₇ and R₄₈ taken together and with the nitrogen to which they are joined are pyrrolidinium, or R₄₇, R₄₈ and R₄₉ taken together and with the nitrogen to which they are joined are pyridinium or quinolinium, wherein each alkyl, hydroxyalkyl and alkyl chain of monosubstituted alkyl independently has 1 to 4 carbon atoms, and alkoxy has 1 to 3 carbon atoms.

Of similar interest are the compounds of Formula VI having the formula

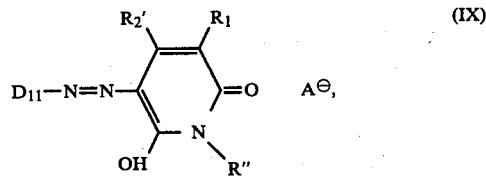

and particularly the compounds of this group wherein R₁ is cyano, and

R₂' is alkyl of 1 to 4 carbon atoms or phenyl.

The most preferred compounds of Formula VI are those having the formula

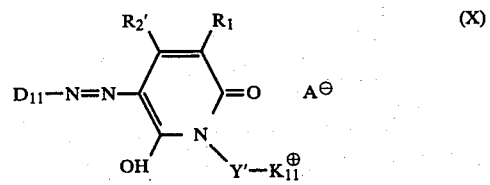

and particularly those of this group wherein R₁ is cyano, and

R₂' is alkyl of 1 to 4 carbon atoms or phenyl, and more particularly the compounds of the formula

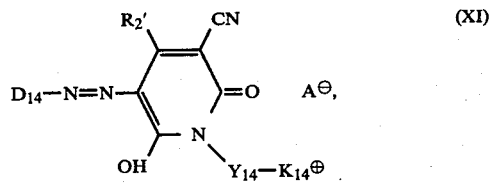

wherein

D₁₄ is phenyl, substituted phenyl or naphthyl, wherein substituted phenyl has 1 to 3 substituents and each substituent is independently chloro, bromo, nitro, cyano, alkyl, alkoxy, phenyl, phenoxy, 4-chlorophenoxy, alkylcarbonylamino, benzamido, alkylcarbonyl, benzoyl, alkylbenzoyl, alkoxycarbonyl, sulfamoyl, alkylsulfamoyl, dialkylsulfamoyl, phenylsulfamoyl, N-alkyl-N-phenylsulfamoyl, phenylcarbamoyl, 2,4-dinitroanilino or phenylazo, R₂' is alkyl or phenyl, Y₁₄ is

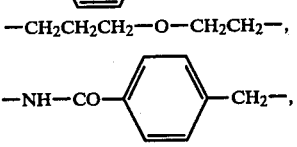

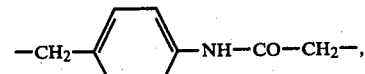

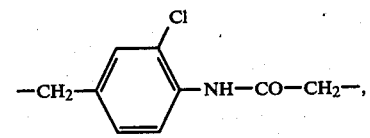

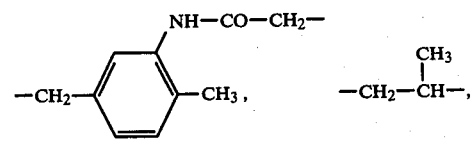

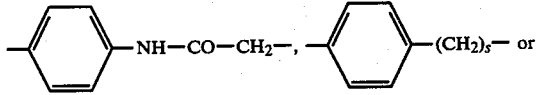

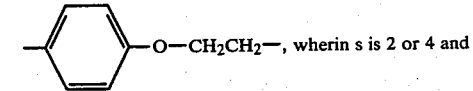

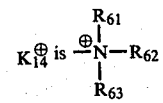 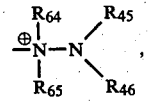

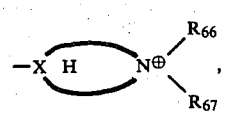, wherein s is 2 or 4 and t is 1 to 2,

K₁₄⊕ is 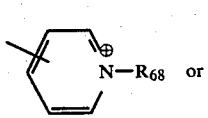

-continued

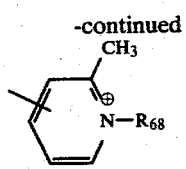

each of $R_{61}$, $R_{62}$, $R_{63}$, $R_{64}$ and $R_{65}$ is independently alkyl or monosubstituted alkyl wherein the substituent of monosubstituted alkyl is hydroxy, cyano or phenyl, each of $R_{45}$ and $R_{46}$ is independently hydrogen or alkyl, or $R_{61}$ and $R_{62}$ taken together and with the nitrogen to which they are joined are pyrrolidinium, piperidinium or morpholinium or $R_{61}$, $R_{62}$ and $R_{63}$ taken together and with the nitrogen to which they are joined are pyridinium, methylpyridinium, quinolinium or

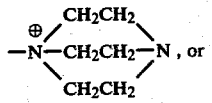

$R_{64}$ and $R_{65}$ taken together and with the nitrogen to which they are joined are pyrrolidinium, piperidinium or morpholinium, or $R_{45}$, $R_{46}$, $R_{64}$ and $R_{65}$ taken together and with the nitrogens to which they are joined are

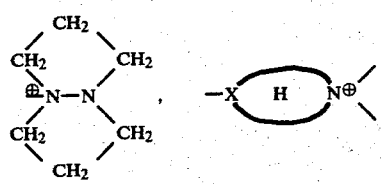

is pyrrolidinium, piperidinium, morpholinium or piperazinium, each of $R_{66}$ and $R_{68}$ is independently alkyl, and $R_{67}$ is alkyl, amino or substituted amino wherein each substituent is independently alkyl, and each alkyl and alkyl chain of each alkylcarbonylamino, alkylcarbonyl, alkylbenzoyl, alkylsulfamoyl, dialkylsulfamoyl, N-alkyl-N-phenylsulfamoyl and monosubstituted alkyl independently has 1 to 4 carbon atoms, and each alkoxy and alkoxy chain of each alkoxycarbonyl independently has 1 to 3 carbon atoms.

Still more preferred are the compounds of Formula XI having the formula

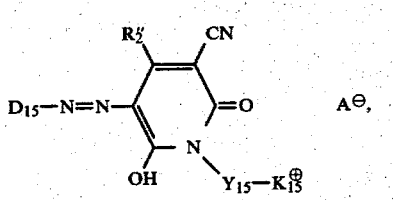

(XII)

wherein $D_{15}$ is phenyl, substituted phenyl or naphthyl, wherein substituted phenyl has 1 to 3 substituents and each substituent of substituted phenyl is independently chloro, bromo, nitro, cyano, methyl, methoxy, ethoxy, phenyl, phenoxy, 4-chlorophenoxy, acetamido, benzamido, acetyl, benzoyl, 4-methylbenzoyl, methoxycarbonyl, ethoxycarbonyl, sulfamoyl, N,N-dimethylsulfamoyl, N-ethyl-N-phenylsulfamoyl, phenylsulfamoyl, phenylcarbamoyl, 2,4-dinitroanilino or phenylazo, $R_2''$ is methyl, ethyl or phenyl, $Y_{15}$ is $-CH_2CH_2-$, $-CH_2CH_2CH_2-$,

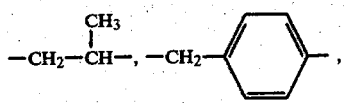

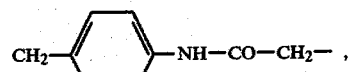

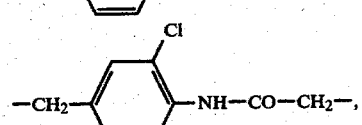

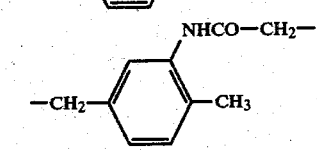

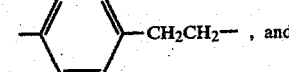

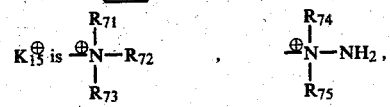

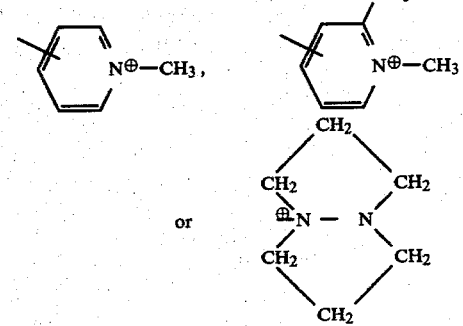

wherein each of $R_{71}$ and $R_{72}$ is independently alkyl of 1 to 4 carbon atoms, 2-hydroxyethyl or 2-cyanoethyl, or $R_{71}$ and $R_{72}$ taken together and with the nitrogen to which they are joined are pyrrolidinium, piperidinium or morpholinium, $R_{73}$ is methyl, ethyl or benzyl, or $R_{71}$, $R_{72}$ and $R_{73}$ taken together and with the nitrogen to which they are joined are pyridinium, 2-methylpyridinium, quinolinium or

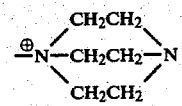

each of $R_{74}$ and $R_{75}$ is independently methyl, ethyl, 2-hydroxyethyl or 2-cyanoethyl, or $R_{74}$ and $R_{75}$ taken together and with the nitrogen to which they are joined are pyrrolidinium, piperidinium or morpholinium, and $A^\ominus$ is an anion.

The most preferred compounds have the formula

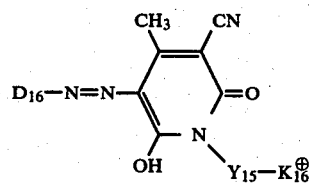
(XIIa)

wherein $D_{16}$ is phenyl, 2-methylphenyl, 3-methylphenyl, 4-methylphenyl, 2,5-dimethylphenyl, 2-methoxyphenyl, 4-methoxyphenyl, 4-ethoxyphenyl, 2-chlorophenyl, 3-chlorophenyl, 4-chlorophenyl, 2,5-dichlorophenyl, 3,4-dichlorophenyl, 2,4,6-trichlorophenyl, 2-bromophenyl, 3-bromophenyl, 2,4,6-tribromophenyl, 3-chloro-4-methoxyphenyl, 2-methyl-4-chlorophenyl, 3-nitrophenyl, 4-nitrophenyl, 2,4-dinitrophenyl, 2-nitro-4-methylphenyl, 2-methyl-5-nitrophenyl, 2-nitro-4-chlorophenyl, 3-nitro-4-chlorophenyl, 2-chloro-4-nitrophenyl, 2,6-dichloro-4-nitrophenyl, 2-methoxy-4-nitrophenyl, 2-methoxy-5-nitrophenyl, 2-cyano-4-chlorophenyl, 2-biphenylyl, 4-biphenylyl, 3-chloro-6-phenoxyphenyl, 4-(4'-chlorophenoxy)phenyl, 4-acetylphenyl, 2-methoxycarbonylphenyl, 4-ethoxycarbonylphenyl, 4-(4'-methylbenzoyl)-phenyl, 4-phenylcarbamoylphenyl, 2-methoxy-5-sulfamoylphenyl, 4-N,N-dimethylsulfamoylphenyl, 4-phenylsulfamoylphenyl, 2-N-ethyl-N-phenylsulfamoylphenyl, 3-phenylsulfamoyl-4-methylphenyl, 4-acetamidophenyl, 3-benzamidophenyl, 4-benzamidophenyl, 4-phenylazophenyl, 4-(2,4-dinitroanilino)phenyl or naphthyl, $Y_{15}$ is

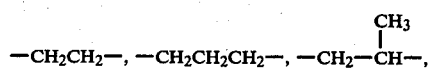

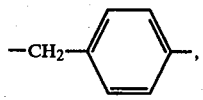

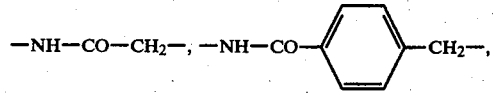

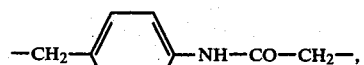

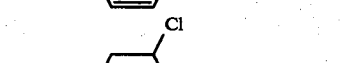

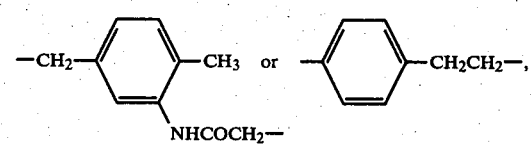

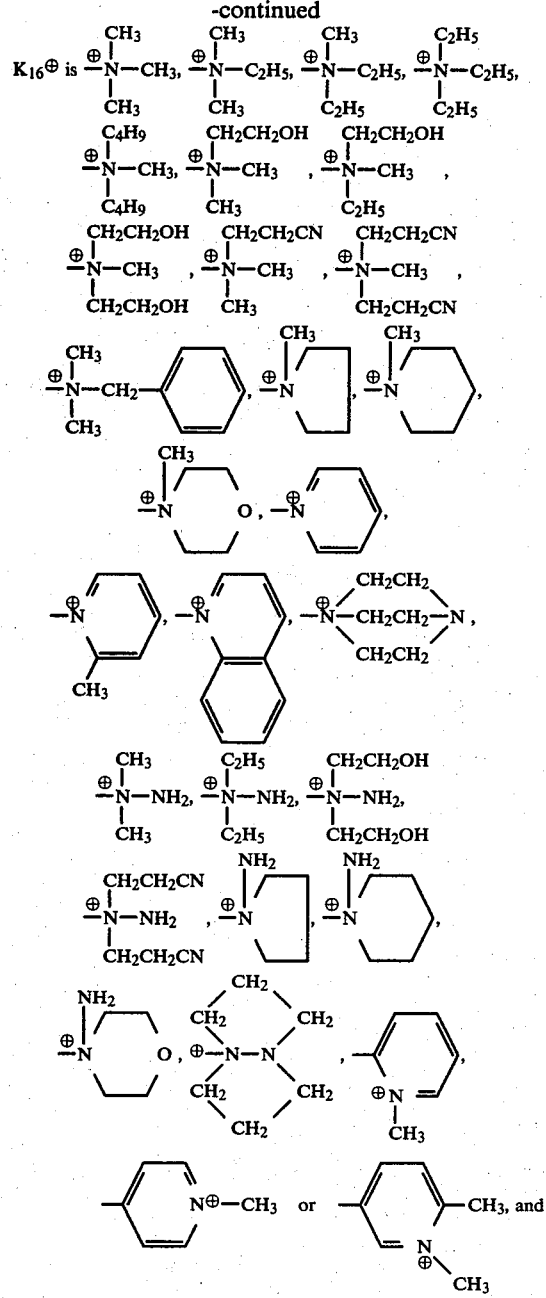

$A^\oplus$ is an anion.

In the preferred compounds, $A^\oplus$ is one of the anions set forth on page 8. However, the chloride and methylsulfate anions are the most preferred ones.

Compounds of the formula

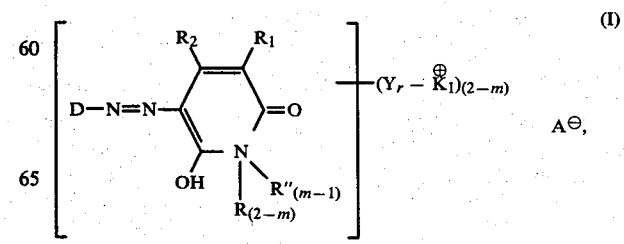
(I)

can be synthesized by diazotizing an amine of the formula D-NH$_2$ and coupling the resulting diazo compound with a compound of the formula

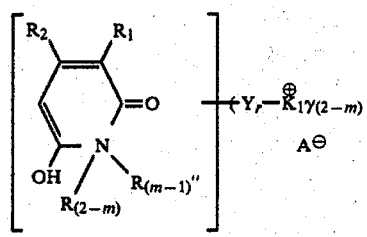 (XIII).

To synthesize compounds wherein m is 1, a compound of the formula D-NH$_2$ and a compound of Formula XIII are selected such that the obtained compound of Formula I has a single group of the formula -Y$_r$-K$_1^\ominus$. The Y$_r$-K$_1^\ominus$ group may be attached to the diazo component D-NH$_2$ or to the coupling component of Formula XIII.

Compounds of the formula

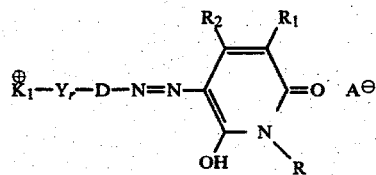 (II)

can be synthesized by diazotizing an amine of the formula K$_1^\oplus$-Y$_r$-D-NH$_2$ and coupling the resulting diazo compound with a compound of the formula

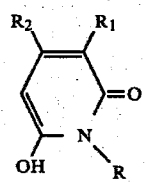 (XIV).

Compounds of the formula

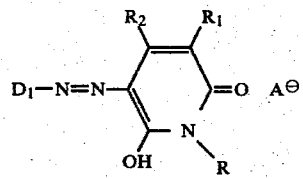 (III)

can be synthesized by quaternizing a compound of the formula

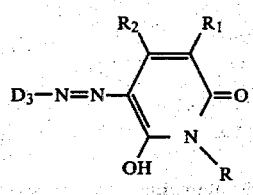 (XV), wherein D$_3$ is

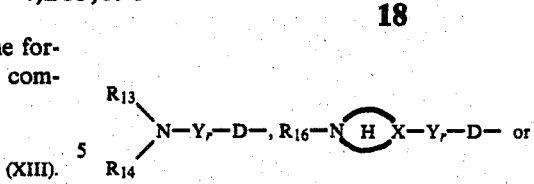

is the radical of an optionally substituted saturated or partially saturated ring, e.g., a 5- or 6-membered ring, and

is the radical of an optionally substituted unsaturated ring, e.g., a 5- or 6-membered ring.

Compounds of the formula

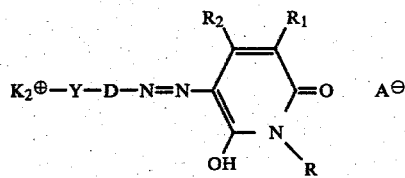 (XVI), wherein K$_2^\oplus$ is

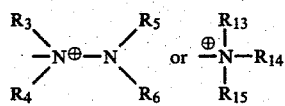

and be synthesized by reacting a compound of the formula

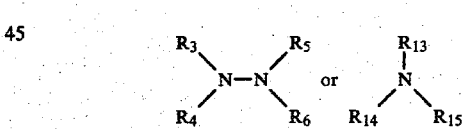

with a compound of the formula

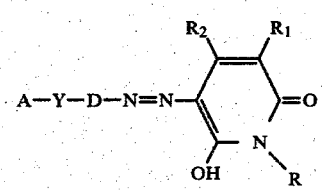 (XVII), wherein

A is a radical that can be converted into an anion. A is preferably halo and most preferably chloro or bromo. A can also be a radical of sulfuric acid, a sulfonic acid or hydrogen sulfide.

Compounds of the formula

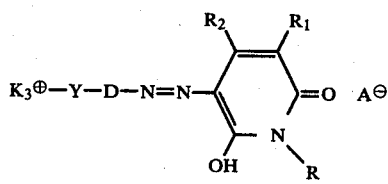

wherein $K_3^\oplus$ is

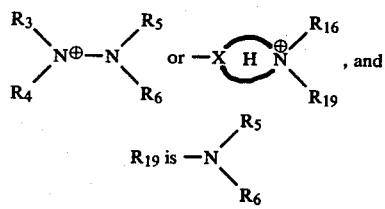, and

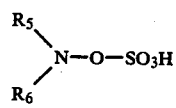

can be synthesized by reacting a compound of the formula $NH_2$-Halogen or

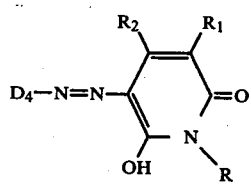

with a compound of the formula

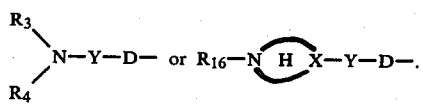 (XIX), wherein $D_4$ is

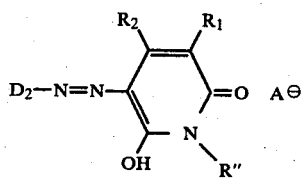

Compounds of the formula

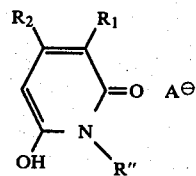 (IV)

can be synthesized by diazotizing an amine of the formula $D_2$-$NH_2$ and coupling the resulting diazo compound with a compound of the formula (XX)

or by quaternizing a compound of the formula

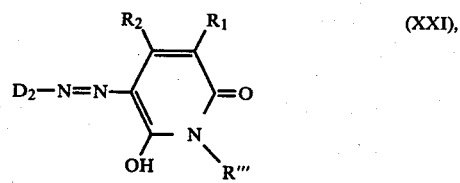 (XXI), wherein $R'''$ is

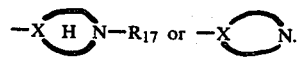

Compounds of the formula

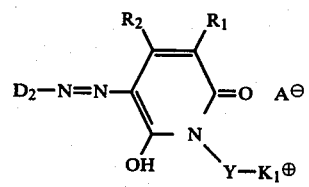 (V)

can be synthesized by diazotizing an amine of the formula $D_2$-$NH_2$ and coupling the resulting diazo compound with a compound of the formula

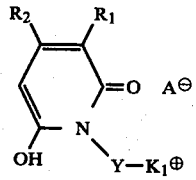 (XXII).

Compounds of the formula

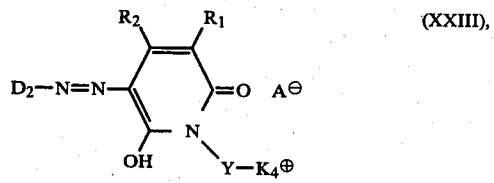 (XXIII), wherein $K_4^\oplus$ is

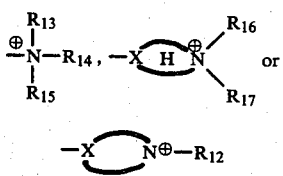

can be synthesized by quaternizing a compound of the formula

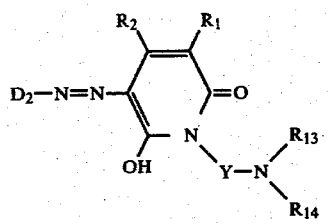
(XXIV)

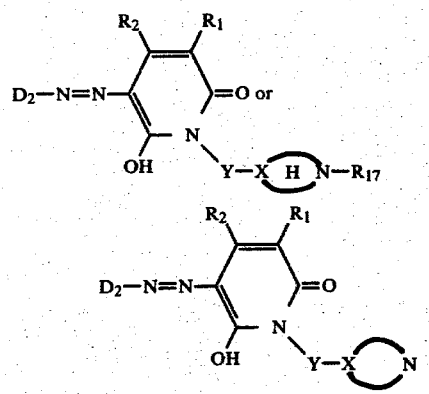
(XXV)

(XXVI)

with a suitable quaternizing agent to yield a compound of the formula

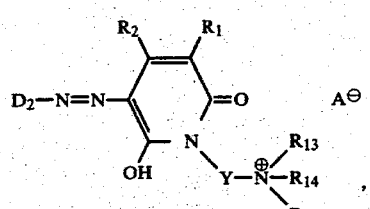
(XXVII)

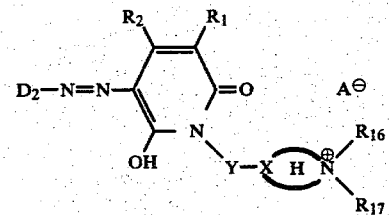
(XXVIII)

or 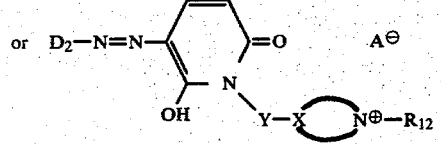
(XXIX)

Compounds of the formula

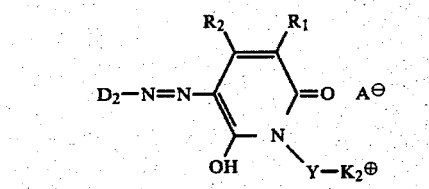
(XXX), wherein $K_2^\oplus$ is

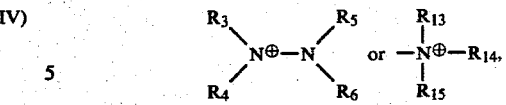
(XXIV)

can be synthesized by reacting a compound of the formula

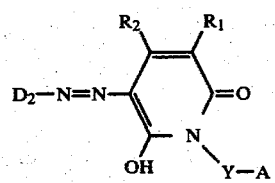
(XXXI), with a compound of the formula

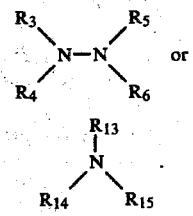

Compounds of the formula

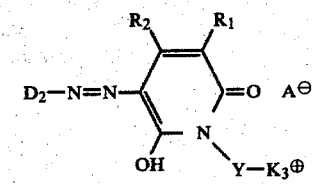
(XXXII), wherein $K_3^\oplus$ is

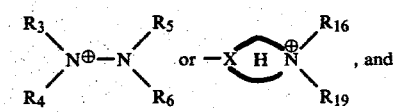, and $R_{19}$ is 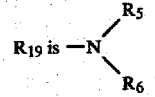

can be synthesized by reacting a compound of the formula

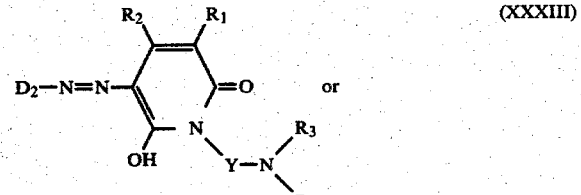
(XXXIII)

-continued

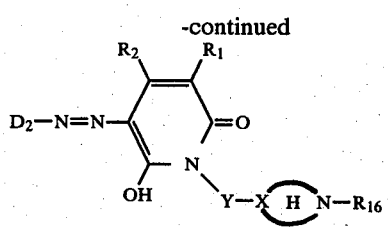

with a compound of the formula NH$_2$-Halogen or

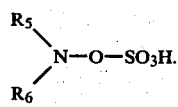

The coupling of diazotized amines of the formula D-NH$_2$, K$_1^\oplus$-Y$_r$-D-NH$_2$ A$^\ominus$ and D$_2$-NH$_2$ with the appropriate coupling components can be carried out by known methods.

Similarly, the quaternization reaction can be effected by known methods. Quaternization can be effected in an inert solvent or aqueous suspension or in an excess of the quaternization agent without a solvent. If necessary, the reaction can be run at an elevated temperature and in a buffered medium. It is advantageous to employ organic acids in combination with a basic compound as needed.

Examples of quaternization agents are alkyl halides (e.g., methyl and ethyl chloride, bromide and iodide), alkyl sulfates (e.g., dimethylsulfate), benzyl chloride, acrylic acid amide hydrochlorides (e.g., CH$_2$=CH-CO-NH$_2$.HCl), chloroacetic acid alkyl esters, β-chloropropionic acid amide and epoxides (e.g., ethylene oxide, propylene oxide and epichlorohydrin). Compounds of the formula R$_{12}$-A, R$_{15}$-A, R$_{16}$-A and R$_{17}$-A are suitable quaternization agents.

A compound of Formula XVII or XXXI can be reacted with a compound of the formula

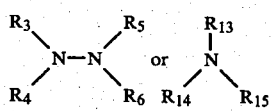

in an organic solvent at a temperature of $-50°-+250°$ C., preferably at a temperature of $-10°-+120°$ C. The reaction can also be carried out at these temperatures in an aqueous medium with the addition of an organic solvent or without any solvent.

A compound of Formula XIX or XXXIII can be reacted with a compound of the formula NH$_2$-Halogen at a temperature of $-50°-+80°$ C. in an organic solvent or in an acid medium adding, if necessary, an organic solvent. Gaseous NH$_2$-Halogen can be added to the reaction mixture or a solution thereof in an organic solvent or water or a mixture thereof can be added to the reaction mixture.

The reaction of a compound of Formula XIX or XXXIII with a compound of the formula

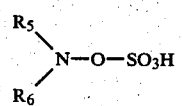

is preferably carried out at a temperature of $-10°-+100°$ C.

The pyridine coupling components, e.g., those of Formulae XIV, XX and XXII can be synthesized by the methods described by J. Guareschi, Atti Accad. R.d. Scienze di Torino, 1895/96; Chem. Ber. 29, 655 (1896); Chem. Zentr. 1896, I, 602; 1896, II, 46; and Umaprasynna Basu, J. Indian Chem. Soc. 8, 319–328 (1931) by condensation of substituted or unsubstituted acetic acid amides or hydrazides with appropriately substituted β-ketocarboxylic acid esters.

The anion A$^\ominus$ of the cationic dyes of this application, e.g., those of Formula I, can be replaced by another anion by means of an ion exchanger or by reaction with salts or acids using, if necessary, a two-step reaction, e.g., by proceeding through the hydroxide or bicarbonate salt.

It is desirable to convert the resulting dyes into stabilized, solid dye preparations or stable, concentrated, aqueous dye solutions.

The new dyes are employed for the dyeing and printing of textiles with consist of or which contain polyacrylonitrile or acrylonitrile copolymer fibers. They are also employed for the exhaust dyeing, pad dyeing and printing of polyamide fibers and polyester fibers modified by the introduction of acid groups. Polyamide fibers of this type are disclosed, for example, in Belgian Pat. No. 706,104. The analogous polyesters are disclosed in U.S. Pat. Nos. 3,018,272 and 3,379,723. It is normally advantageous to dye from an aqueous neutral or acid medium at a temperature of 60°–100° C. or at a temperature above 100° C. under static pressure. Level dyeings are obtained without the assistance of retarders. Blend fabrics containing a component of acrylic fiber can be successfully dyed with these dyes. The dyes of the present invention which have good solubility in organic solvents are also suitable for the mass pigmentation of natural and synthetic resins and plastics. It has been found that mixtures of two or more of the new dyes or mixtures of these and cationic dyes can be successfully applied, i.e., the dyes are well suited for combined application. They can also be employed for dyeing paper and leather.

Level dyeings of good light and wet fastness are obtained on polyacrylonitrile and acrylonitrile copolymer fibers as well as on the aforenamed substrates. The high tinctorial strength of the new dyes is a noteworthy feature.

The dye of the formula

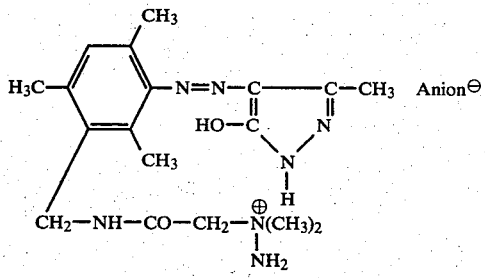

disclosed in Belgian Pat. No. 633,447 is employed for, among other purposes, dyeing polyacrylonitrile fibers. In comparison with it the dyes of Formula I build up more powerfully on polyacrylonitrile fibers, giving dyeings of greater depth and of superior light fastness.

Dyeings produced with dyes of Formula I have good fastness to washing, perspiration, sublimation, pleating, decatizing, pressing, steaming, water, sea water, dry cleaning, cross dyeing and solvents. They show good compatibility with salts, are well soluble, especially in water, have good stability to pH conditions and boiling, and reserve natural and synthetic polyamide fibers.

It is assumed that the compounds bearing a dihydroxypyridone radical are present in a tautomeric state, as exemplified by the following formulae:

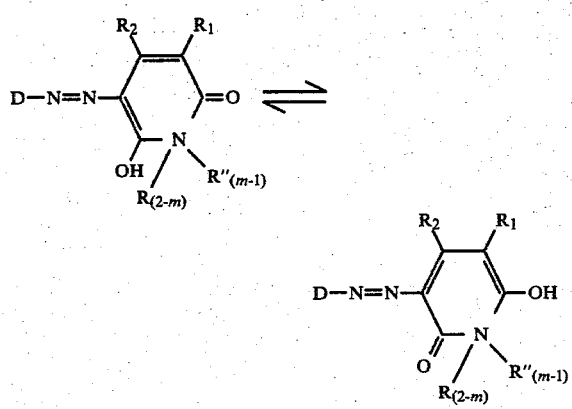

In the following Examples the parts and percentages are by weight and the temperature in degrees centigrade.

EXAMPLE 1

34 Parts of 4-amino-4'-(ω-pyridinium)-acetaminodiphenyl (prepared by reacting 4-amino-4'-chloroacetaminodiphenyl with pyridine) are diazotized with 6.9 parts of sodium nitrite by the normal method. At 0° the mixture is adjusted to pH 7.5 with hydrated sodium carbonate, after which a solution of 16 parts of 2,6-dihydroxy-4-methyl-5-cyanopyridine in 200 parts of water, also of pH 7.5, is added dropwise. The reaction mixture is raised to 35° and the dye is precipitated with hydrochloric acid and sodium chloride, filtered off, washed with aqueous sodium chloride solution, dried and ground. The new dye is obtained as a powder which dissolves in water and is applicable to polyacrylonitrile fibres, on which it gives orange-red dyeings having excellent fastness properties.

EXAMPLE 2

17.8 Parts of 4-amino-ω-dimethylamino-acetophenone (prepared by reacting 4-acetamino-ω-chloracetophenone with dimethylamine and saponifying the acetamino group with hydrochloric acid) are diazotized at 0° by the normal method. The pH is adjusted to 8.0 with sodium carbonate and over one hour a solution of 17 parts of 2,6-dihydroxy-4-methyl-5-cyanopyridine in 200 parts of water, likewise of pH 8.0, is dropped in. On completion of coupling the separated dye is filtered off, washed with water, dried and ground. 17 Parts of the powdered dye are stirred into a mixture of 400 parts of chlorobenzene and 50 parts of N-methylpyrrolidone-(2) at 120°, and at the same temperature 15 parts of dimethyl sulphate are added in the course of one hour. After a further 2 hours at 120° the reaction mixture is cooled to 40° and the dye filtered off, washed with acetone and purified by recrystallization, e.g., from glacial acetic acid. The new dye is well soluble in water and is suitable for dyeing polyacrylonitrile fibres in fast greenish yellow shades. In place of dimethylamine the equivalent amount of pyrrolidine can be employed using the same procedure as above to obtain a similar dye.

EXAMPLE 3

24.85 Parts of 1-amino-4-methylbenzene-5-sulphonic acid-(2'-chloro)ethylamide (prepared by reduction of 1-nitro-4-methylbenzene-5-sulphonic acid-2'-chlorethylamide) are diazotized with 6.9 parts of sodium nitrite at 0° by the normal method. The diazo solution is adjusted to pH 8.0 with sodium carbonate. A solution, also of pH 8.0, of 17 parts of 2,6-dihydroxy-4-methyl-5-cyanopyridine in 200 parts of water is then added in the course of 1 hour. When coupling is complete the precipitated dye is filtered off, washed with water and dried with vacuum. It is added to a mixture of 9 parts of N,N-dimethylhydrazine and 120 parts of dimethylformamide at 50°, on which the mixture is allowed to cool to 20°. The dye settles out and is filtered off and washed with acetone. As thus obtained, the dye melts at 273°–275°, is soluble in water and gives greenish yellow dyeings of excellent fastness on polyacrylonitrile fibres.

Dyeing Method

One part of the dye of Example 1 and one part of 40% acetic acid are pasted, 400 parts of distilled water at 60° are run over the paste with constant stirring and with boiling for a short time to complete dissolving. The solution is added to 7600 parts of distilled water, with the subsequent addition of 2 parts of glacial acetic acid. 100 Parts of a fabric of polyacrylonitrile fibre are entered into this dyebath at 60°, after previous treatment for 10–15 minutes at 60° in a bath of 8000 parts of water and 2 parts of glacial acetic acid. The dyebath is raised to 100° over 30 minutes and held at the boil for 1 hour. On removal the fabric is washed off. A level orange-red dyeing is obtained which has excellent light and very good wet fastness properties.

EXAMPLE 4

22.8 Parts of 4-amino-ω-N,N,N-trimethylammonium chloride-acetophenone in 200 parts of 4% hydrochloric acid are diazotized with 6.9 parts of sodium nitrite at 0° by the normal method. After adjustment to pH 4.5 with sodium acetate, the solution is coupled with 21.3 parts of 1-(2'-hydroxyethyl)-2-keto-3-cyano-4-methyl-6-hydroxy-1,2-dihydropyridine. The dye is obtained as a water-soluble powder. It is suitable for dyeing polyacrylonitrile fibres, on which it gives fast greenish yellow dyeings. Similar dyeings showing the same good fastness properties as the dye of Example 4 are obtained when the 21.3 parts of 1-(2'-hydroxyethyl)-2-keto-3-cyano-4-methyl-6-hydroxy-1,2-dihydropyridine are replaced by the equivalent amount of 1-(3'-dimethylaminopropyl-2-keto-3-cyano-4-methyl-6-hydroxy-1,2-dihydropyridine, 1-benzyl-2-keto-3-cyano-4-methyl-6-hydroxy-1,2-dihydropyridine, 1-methyl-2-keto-3-cyano-4-phenyl-6-hydroxy-1,2-dihydropyridine, 1-(2'-morpholinylethyl)-2-keto-3-cyano-4-methyl-6-hydroxy-1,2-dihydropyridine, 1-[4'-ω'''-dimethylamino-ethoxy]-phenyl-2-keto-3-cyano-4-methyl-6-hydroxy-1,2-dihydropyridine, 1-(3'-methoxypropyl)-2-keto-3-cyano-6-hydroxy-1,2-dihydropyridine, 1-[2'-pyridinyl-(2)]-ethyl-2-keto-3-cyano-4-methyl-6-hydroxy-1,2-dihydropyridine, 1-dimethylamino-2-keto-3-cyano-4-methyl-6- hydroxy-1,2-dihydropyridine or 1-amino-2-keto-3-cyano-4-methyl-6-hydroxy-1,2-dihydropyridine.

EXAMPLE 5

13.7 Parts of nitrosylsulphuric acid are added at 0° over one hour to a solution of 10 parts of 2-aminothiazole in 100 parts of sulphuric acid of 16° Tw. The resulting diazo solution is run onto 150 parts of ice and the excess acid decomposed with aminosulphonic acid. In the course of one hour a solution of 25.9 parts of 1-(3'-dimethylaminopropyl)-propyl-2-keto-3-cyano-4-methyl-6-hydroxy-1,2-dihydropyridine in 50 parts of water is added dropwise to the diazo solution, followed by 60 parts of common salt. The dye is isolated in the normal manner. On drying and grinding it is obtained as a water-soluble powder which is highly suitable for dyeing polyacrylonitrile fibres in fast, neutral yellow shades. Similar dyes showing equally good fastness properties are obtained when the 25.9 parts of 1-(3'-dimethyl-aminopropyl)-propyl-2-keto-3-cyano-4-methyl-6-hydroxy-1,2-dihydropyridine used in Example 5 are replaced by the equivalent amount of 1-(3'-dimethyl-aminopropyl)-propyl-2-keto-3-cyano-4-phenyl-6-hydroxy-1,2-dihydropyridine, 1-[4'-(ω''-dimethylamino)-acetamino]-phenyl-2-keto-3-cyano-4-methyl-6-hydroxy-1,2-dihydropyridine, 1-[2'-pyridinyl-(2)]-ethyl-2-keto-3-cyano-4-methyl-6-hydroxy-1,2-dihydropyridine, 1-[2'-pyridinyl-(4)]-ethyl-2-keto-3-cyano-4-phenyl-6-hydroxy-1,2-dihydropyridine, 1-dimethylamino-2-keto-3-cyano-4-methyl-6-hydroxy-1,2-dihydropyridine or 1-amino-2-keto-3-cyano-4-methyl-6-hydroxy-1,2-dihydropyridine, or by replacing the diazo component by an equivalent amount of 2-amino-1,2,4-triazolone, 3-methyl-5-amino-1,2,4-triazole, 3-aminoindazole, 4-methyl-3-aminoindazole, 2-amino-1,3,4-thiadiazole, 2-amino-4-methyl-1,3,4-thiadiazole, 2-amino-5-methyl-1,3,4-thiadiazole, ω-dimethylamino-4-aminoacetophenone, 2'-dimethylamino-4-aminopropiophenone, 1-(ω-dimethylamino)-acetamino-4-aminobenzene or 1-(ω-diethylamino)-acetamino-4-aminobenzene.

EXAMPLE 6

34.6 Parts of the dye of Example 5, which has the formula

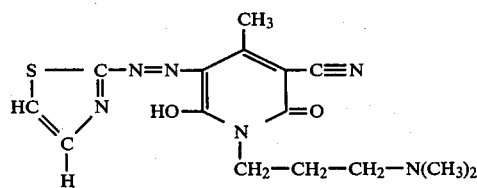

are dissolved in 750 parts of chlorobenzene and quaternized with 50 parts of dimethyl sulphate in the presence of 4 parts of magnesium oxide. The dye salt is filtered off and purified by washing with acetone followed by recrystallization. The new dye is water-soluble and gives fast, neutral yellow dyeings on polyacrylonitrile fibres. Equally good dyes are obtained when the compounds named in Example 5 are employed and quaternated as stated in Example 6.

EXAMPLE 7

19.85 Parts of 1-amino-4-(2'-chloropropionyl)-aminobenzene are dissolved in 200 parts of 60% hydrochloric acid and diazotized with 6.9 parts of sodium nitrite at 0° by the known method. A solution of 18 parts of 1,4-dimethyl-2-keto-3-cyano-6-hydroxy-1,2-dihydropyridine is dropped into the diazonium solution, and at the same time a 20% aqueous solution of 14 parts of crystallized sodium acetate is added. The dye settles out and is collected on a filter, washed and dried. It is then dissolved in 800 parts of chlorobenzene and quaternized with 9 parts of N,N-dimethylhydrazine at 110°. The new dye is suitable for dyeing polyacrylonitrile fibres in fast yellow shades. Dyes of similarly good quality are obtained when the 9 parts of dimethylhydrazine in this Example are replaced by the equivalent amount of trimethylamine, triethylamine, pyridine or quinoline, or when the 19.85 parts of 1-amino-4-(2'-chloropropionyl)-aminobenzene are replaced by the equivalent amount of 1-amino-4-(ω'-chloracetamino)-benzene, 1-amino-2-methyl-4-(ω'-chloracetamino)-5-methoxybenzene, 1-amino-2-nitro-4-(ω'-chloracetamino)-benzene or 1-amino-4-(ω'-chloro)-acetylbenzene.

EXAMPLE 8

17.25 Parts of 1-amino-2-nitro-4-chlorobenzene are diazotized in the known way. 21.3 Parts of 1-(2'-hydroxyethyl)-2-keto-3-cyano-4-methyl-6-hydroxy-1,2-dihydropyridine dissolved in 50 parts of glacial acetic acid are dropped into the hydrochloric acid diazo solution of crystallized sodium acetate are added dropwise. The dye thus formed is then dissolved in a mixture of 800 parts of toluene and 70 parts of dimethylformamide. Over one hour 13.2 parts of thionyl chloride are added to the solution, following which the temperature of the reaction mixture is raised to 105°. Subsequently, it is cooled to 40° and 9 parts of N,N-dimethylhydrazine are added. The reaction is then conducted further for 5 hours a 105°. The dye settles out and is collected on a filter, dried and purified by recrystallization. It is well soluble in water and is applicable to polyacrylonitrile fibres, on which it gives fast greenish yellow dyeings. Very similar dyes of equally good quality are obtained when the 17.2 parts of 1-amino-2-nitro-4-chlorobenzene employed in this Example are replaced by the equivalent amount of 1-amino-3-nitro-4-chlorobenzene, 1-amino-2-nitro-4-methylbenzene, 1-aminobenzene-4-sulphodimethylamide, 1-amino-4-acetylbenzene, 4-aminobenzoic acid ethyl ester, 1-amino-2,5-dichlorobenzene or 1-amino-2,4-dinitrobenzene or when the 9 parts of N,N-dimethylhydrazine are replaced by the equivalent amount of trimethylamine, triethylamine, N-methyl-N,N-diethylamine, N-methyl-N,N-di-(β-hydroxyethyl)-amine, triethylenediamine, pyridine, N-methylpiperidine, N-methylpyrrolidine, N-methylmorpholine, N,N-dimethyl-N-β-hydroxyethylamine, N-methyl-N-ethyl-N-β-hydroxyethylamine, N-ethyl-N,N-dimethylamine, 2-methylpyridine, quinoline, diethylhydrazine, N,N-di-(β-hydroxyethyl)-hydrazine, N-aminopyrrolidine, N-aminopiperidine, N-aminomorpholine, N,N-di-(β-cyanoethyl)hydrazine or

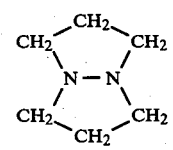

Any of these amines may occur in any of the other dyes of the invention in the form of their cationic structure.

EXAMPLE 9

A solution of 37.4 parts of the compound of the formula

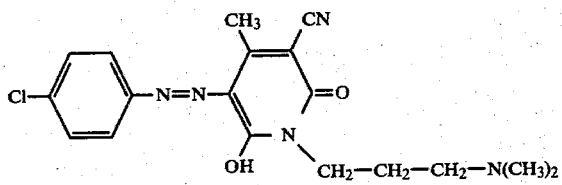

in 500 parts of chlorobenzene is prepared and combined with 50 parts of dimethyl sulphate at 120°. The compound is quaternized at 130°, after which the reaction mixture is cooled to room temperature and the separated dye filtered off, washed with acetone and dried. It is obtained as a yellow powder which is well soluble in water and is excellent for dyeing polyacrylonitrile fibres.

Dyes of comparably good quality are obtained when the quaternization step in the above procedure is carried out with diethyl sulphate, chloramine or hydroxylamine-O-sulphonic acid.

The starting compound used can be prepared by coupling diazotized 1-amino-4-chlorobenzene with 1-(3'-dimethylaminopropyl)-propyl-2-keto-3-cyano-4-methyl-6-hydroxy-1,2-dihydropyridine.

EXAMPLE 10

13.5 Parts of 1-amino-4-acetylbenzene are diazotized in the normal way in 200 parts of 6% ice-cold hydrochloric acid. A solution of 40 parts of 1-(3'-N',N',N'-trimethylammoniumpropyl)-2-keto-3-cyano-4-methyl-6-hydroxy-1,2-dihydropyridine-methylsulfate in 150 parts of water is dropped into the diazo solution at 0° in the course of one hour. At the same time 200 parts of a 14% aqueous solution of crystallized sodium acetate are added. Following coupling, the dye is converted into the chloride with sodium chloride and salted out, filtered off, washed, dried and ground. It is a yellow powder which dissolves in water and is dyeable on polyacrylonitrile fibres, on which it gives fast, greenish yellow dyeings.

The 40 parts of 1-(3'-N',N',N'-trimethylammoniumpropyl)-2-keto-3-cyano-4-methyl-6-hydroxy-1,2-dihydropyridine used in this Example can be replaced by the equivalent amount of 1-[2'-N-methylpyridinium-(2)⊕Cl⊖]-ethyl-2-keto-3-cyano-4-methyl-6-hydroxy-1,2-dihydropyridine or 1-[2'-(N-methylmorpholinium⊕-Cl⊖)]-ethyl-2-keto-3-cyano-4-methyl-6-hydroxy-1,2-dihydropyridine, to obtain dyes possessing similar excellent properties.

EXAMPLE 11

Diazotization of 12.32 parts of 1-amino-2-methoxybenzene is carried out by the known method and to the ice-cold mineral acid diazo solution a solution of 25 parts of 1-(3'-dimethylaminopropyl)-2-keto-3-cyano-4-methyl-6-hydroxy-1,2-dihydropyridine in 80 parts of water is added with stirring. Stirring is continued at 0°. The dye formed is salted out at 80° with sodium chloride, filtered off and dried. 36.9 parts of the dye are dissolved in 500 parts of chlorobenzene at 100°, 26 parts of dimethyl sulphate are added to the solution at the same temperature and it is then stirred for a further 5 hours at 100°. On cooling the precipitated salt of the quaternized dye is collected on a filter and washed with chloroform and petroleum ether. Applied from aqueous medium, this salt gives dyeings of bright reddish yellow shade on polyacrylonitrile fibres which show high light and wet fastness.

An analogous dye is obtained when in place of diethyl sulphate 35 parts of benzyl chloride are employed.

In place of the 25 parts of 1-(3'-dimethylaminopropyl)-2-keto-3-cyano-4-methyl-6-hydroxy-1,2-dihydropyridine an equivalent amount of a compound of the formula

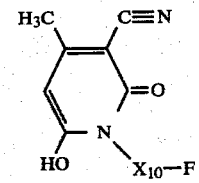

can be employed, the operating procedure being otherwise as given in this Example.

These two alternatives yield quaternized dyes with similarly good properties, in which $X_{10}$ stands for:

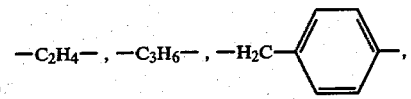

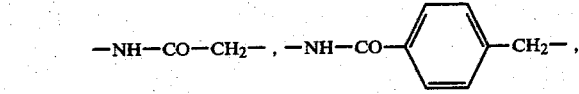

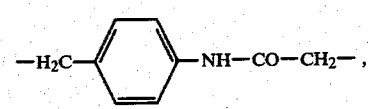

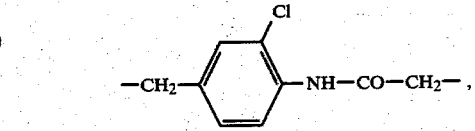

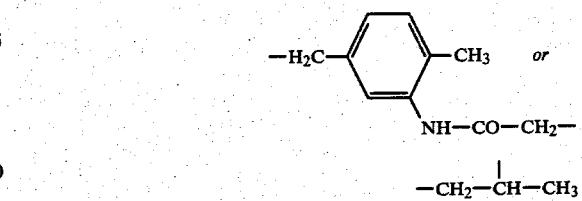

and F stands for one of the radicals listed in Table A. In any given dye these groupings can be exchanged for any other one of the stated groupings.

EXAMPLE 12

23.3 Parts of 4-amino-3-methylbenzoic acid-3'-dimethylamino-n-propylamide are diazotized in the normal way and the hydrochloric acid diazo solution is entered into an ice-cold aqueous suspension of 26.2 parts of 1-methyl-2-keto-3-cyano-4-methyl-6-hydroxy-1,2-dihydropyridine. The pH of the reaction mixture is adjusted to 3.0 by dropping in 50% aqueous acetate solution. Subsequently the dye is salted out with common salt, collected on a filter and dried. It is water-soluble and gives fast greenish yellow dyeings on polyacrylonitrile fibres.

For conversion into a quaternary salt this dye is treated with 4 parts of magnesium oxide and 30 parts of dimethyl sulphate in 500 parts of chloroform. After quaternization, a mixture of 1,000 parts of water and 12 parts of 30% hydrochloric acid is run into the reaction mixture and the chloroform distilled off at the same time. The solution is filtered while hot and the dye then salted with common salt, filtered off as the chloride and washed with dilute sodium chloride solution. On drying and grinding it is obtained as a yellow powder which is applicable from an aqueous bath to polyacrylonitrile fibres to give greenish yellow dyeings of high light and wet fastness.

A similarly good dye is obtained when the tertiary amino group of the aforedescribed dye is converted into the quaternary form by means of toluenesulfonic acid methyl ester instead of dimethyl sulphate.

Dyes of the same high quality are obtained when the 23.3 parts of 4-amino-3-methyl-benzoic acid-3'-dimethylamino-n-propylamide used in this Example are replaced by the equivalent amount of the diazo compound of an amine of the formula

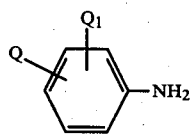

where Q represents a radical of formula

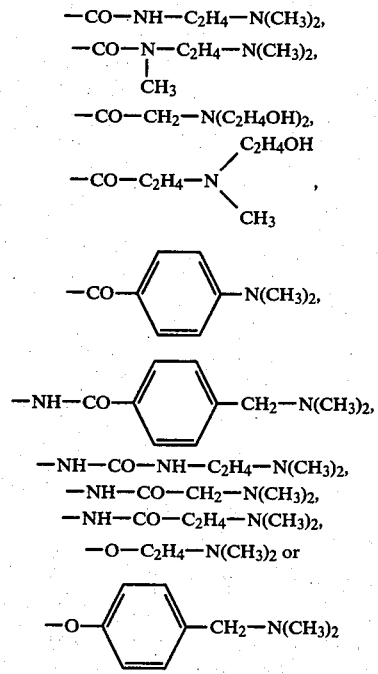

and $Q_1$ represents hydrogen, chlorine, bromine, methyl, ethyl, methoxy, ethoxy or phenoxy, with a coupling component of the formula

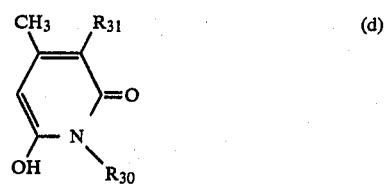

with subsequent quaternization, where $R_{30}$ represents methyl, ethyl, phenyl or cyclohexyl and $R_{31}$ stands for hydrogen or —CN. The coupling compound, wherein $R_{31}$ stands for hydrogen may be obtained by splitting off the —CN group from compounds of formula (d) in strong acid medium.

EXAMPLE 13

At 0°–5° 30 parts of 23% sodium nitrite solution are run into a suspension of 17.23 parts of 1-amino-3-nitro-4-chlorobenzene in 200 parts of 6% hydrochloric acid. The resulting diazo solution is diluted with 200 parts of ice-water and to it is added an aqueous hydrochloric acid solution of 24 parts of 1-(3'-N',N'-dimethylaminopropyl)-2-keto-3-cyano-4-methyl-6-hydroxy-1,2-dihydropyridine.

After coupling, the dye formed is precipitated with sodium chloride in the form of the hydrochloride, collected on a filter and dried. It can be purified by recrystallization, e.g., from acetic acid. It is ground to a yellow powder which dissolves in water and dyes polyacrylonitrile fibres in bright yellow shades of good light and wet fastness. The thus obtained dye is quaternized with dimethylsulphate according to Example 12.

For the preparation of 1-(3'-N',N'-dimethylaminopropyl)-2-keto-3-cyano-4-methyl-6-hydroxy-1,2-dihydropyridine, cyanoacetic ester is reacted with 3-dimethylaminopropylamine by the known method to give cyanoacetic acid-3-dimethylaminopropylamide and this is condensed in the known way to 1-(3'-N',N'-dimethylaminopropyl)-2-keto-3-cyano-4-methyl-6-hydroxy-1,2-dihydropyridine.

Dyeing Example

A mixture of 20 parts of the dye of Example 13 and 80 parts of dextrin is ground in a ball mill for 48 hours. One part of the resulting preparation and one part of 40% acetic acid are pasted and dissolved in 200 parts of demineralized water with boiling. The solution is added to 7000 parts of softened water and the bath set with 2 parts of glacial acetic acid. 100 Parts of a polyacrylonitrile fabric are entered into the bath at 60°. The material may be pretreated for 10–15 minutes at 60° in a bath of 8000 parts of water and 2 parts of glacial acetic acid. The dyebath is raised to 98°–100° in 30 minutes and held at the boil for 1½ hours. A yellow dyeing of good light and wet fastness is obtained.

The following table shows the structural composition of further dyes which can be produced in accordance with the procedure of Examples 12 and 13. These dyes have the formula

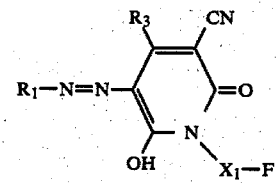

where $R_1$, $R_3$, $X_1$ and F have one of the meanings stated in the table. The symbol F may stand for any one of the amines F listed in Table A. In any given dye these groups may be replaced by any other one of the stated groups. The amines are quaternized with dimethylsulphate according to the details given in Examples 12 and 13.

Table A

F may stand for any one of the symbols $F_1$ to $F_{23}$ which represent the groupings listed below.

Table A

| | | |
|---|---|---|
| $F_1$ | represents | $-NH_2$ |
| $F_2$ | represents | $-NH-CH_3$ |
| $F_3$ | represents | $-NH-C_2H_5$ |
| $F_4$ | represents | $-NH-C_2H_4-OH$ |
| $F_5$ | represents | $-NH-C_2H_4-CN$ |
| $F_6$ | represents | $-NH-CH_2-CHOH-CH_2-OH$ |
| $F_7$ | represents | $-NH-C_3H_7(n)$ |
| $F_8$ | represents | $-NH-C_4H_9(n)$ |
| $F_9$ | represents | $-N(CH_3)_2$ |
| $F_{10}$ | represents | $-N(C_2H_5)_2$ |
| $F_{11}$ | represents | $-N(C_4H_9)_2(n)$ |
| $F_{12}$ | represents | morpholino (–N(CH₂CH₂)₂O) |
| $F_{13}$ | represents | piperidino |
| $F_{14}$ | represents | $-N(CH_3)(C_2H_4CN)$ |
| $F_{15}$ | represents | $-N(C_2H_4CN)_2$ |
| $F_{16}$ | represents | $-N(C_2H_4OH)_2$ |
| $F_{17}$ | represents | piperazino (–N(CH₂CH₂)₂NH) |
| $F_{18}$ | represents | 4-methylsulphonyl-piperazino (–N(CH₂CH₂)₂N–SO₂CH₃) |
| $F_{19}$ | represents | pyridyl |
| $F_{20}$ | represents | pyridyl |
| $F_{21}$ | represents | methylpyridyl |
| $F_{22}$ | represents | $-C(=NH)NH_2$ |
| $F_{23}$ | represents | 4-methyl-piperazino (–N(CH₂CH₂)₂N–CH₃) |

| Ex. No. | $R_1$ | $X_1$ | F | $R_3$ | Shade of dyeing on polyacrylonitrile |
|---|---|---|---|---|---|

Table A-continued

| | | | | | |
|---|---|---|---|---|---|
| 14 | NO$_2$-phenyl (3-nitrophenyl) | —C$_2$H$_4$— | F$_1$ | —CH$_2$—C$_6$H$_5$ | yellow |
| 15 | " | " | F$_9$ | —C$_2$H$_5$ | " |
| 16 | " | —C$_3$H$_6$— | F$_9$ | " | " |
| 17 | 6-Methylsulphonyl-benzothiazolyl-2 | " | F$_9$ | —CH$_3$ | " |
| 18 | NO$_2$, Cl-phenyl (4-chloro-2-methyl-5-nitrophenyl) | —C$_2$H$_4$— | F$_1$ | —CH$_3$ | " |
| 19 | " | " | F$_2$ | " | " |
| 20 | " | " | F$_3$ | " | " |
| 21 | " | " | F$_4$ | " | " |
| 22 | " | " | F$_5$ | " | " |
| 23 | " | " | F$_6$ | " | " |
| 24 | " | " | F$_7$ | " | " |
| 25 | " | " | F$_8$ | " | " |
| 26 | " | " | F$_9$ | " | " |
| 27 | " | " | F$_{10}$ | " | " |
| 28 | " | " | F$_{11}$ | " | " |
| 29 | " | " | F$_{12}$ | " | " |
| 30 | " | " | F$_{13}$ | " | " |
| 31 | " | " | F$_{14}$ | " | " |
| 32 | " | " | F$_{15}$ | " | " |
| 33 | " | " | F$_{16}$ | " | " |
| 34 | " | " | F$_{17}$ | " | " |
| 35 | " | " | F$_{18}$ | " | " |
| 36 | " | " | F$_{19}$ | " | " |
| 37 | " | " | F$_{20}$ | " | " |
| 38 | " | " | F$_{21}$ | " | " |
| 39 | " | " | F$_{22}$ | " | " |
| 40 | " | " | F$_{23}$ | " | " |
| 41 | " | —CH$_2$—CH$_2$—CH$_2$— | F$_1$ | " | " |
| 42 | " | " | F$_2$ | " | " |
| 43 | " | " | F$_3$ | " | " |
| 44 | " | " | F$_4$ | " | " |
| 45 | " | " | F$_5$ | " | " |
| 46 | " | " | F$_6$ | " | " |
| 47 | " | " | F$_7$ | " | " |
| 48 | " | " | F$_8$ | " | " |
| 49 | " | " | F$_9$ | " | " |
| 50 | " | " | F$_{10}$ | " | " |
| 51 | " | " | F$_{11}$ | " | " |
| 52 | " | " | F$_2$ | " | " |
| 53 | " | " | F$_{13}$ | " | " |
| 54 | " | " | F$_{14}$ | " | " |
| 55 | " | " | F$_{15}$ | " | " |
| 56 | " | " | F$_{16}$ | " | " |
| 57 | " | " | F$_{17}$ | " | " |
| 58 | " | " | F$_{18}$ | " | " |
| 59 | " | " | F$_{19}$ | " | " |
| 60 | " | " | F$_{20}$ | " | " |
| 61 | " | " | F$_{21}$ | " | " |
| 62 | " | " | F$_{22}$ | " | " |
| 63 | " | " | F$_{23}$ | " | " |
| 64 | " | —C$_2$H$_4$— | F$_1$ | —C$_6$H$_5$ (phenyl) | " |
| 65 | " | " | F$_2$ | " | " |
| 66 | " | " | F$_3$ | " | " |
| 67 | " | " | F$_4$ | " | " |
| 68 | " | " | F$_5$ | " | " |
| 69 | " | " | F$_6$ | " | " |
| 70 | " | " | F$_7$ | " | " |
| 71 | " | " | F$_8$ | " | " |
| 72 | " | " | F$_9$ | " | " |
| 73 | " | " | F$_{10}$ | " | " |
| 74 | " | " | F$_{11}$ | " | " |
| 75 | " | " | F$_{12}$ | " | " |
| 76 | " | " | F$_{13}$ | " | " |
| 77 | " | " | F$_{14}$ | " | " |
| 78 | " | " | F$_{15}$ | " | " |
| 79 | " | " | F$_{16}$ | " | " |
| 80 | " | " | F$_{17}$ | " | " |
| 81 | " | " | F$_{18}$ | " | " |
| 82 | " | " | F$_{19}$ | " | " |
| 83 | " | " | F$_{20}$ | " | " |
| 84 | " | " | F$_{21}$ | " | " |
| 85 | " | " | F$_{22}$ | " | " |
| 86 | " | " | F$_{23}$ | " | " |

Table A-continued

| No. | | Group | F | | |
|---|---|---|---|---|---|
| 87 | " | —CH$_2$—CH$_2$—CH$_2$— | F$_1$ | " | " |
| 88 | " | " | F$_2$ | " | " |
| 89 | " | " | F$_3$ | " | " |
| 90 | " | " | F$_4$ | " | " |
| 91 | " | " | F$_5$ | " | " |
| 92 | " | " | F$_6$ | " | " |
| 93 | " | " | F$_7$ | " | " |
| 94 | " | " | F$_8$ | " | " |
| 95 | " | " | F$_9$ | " | " |
| 96 | " | " | F$_{10}$ | " | " |
| 97 | " | " | F$_{11}$ | " | " |
| 98 | " | " | F$_{12}$ | " | " |
| 99 | " | " | F$_{13}$ | " | " |
| 100 | " | " | F$_{14}$ | " | " |
| 101 | " | " | F$_{15}$ | " | " |
| 102 | " | " | F$_{16}$ | " | " |
| 103 | " | " | F$_{17}$ | " | " |
| 104 | " | " | F$_{18}$ | " | " |
| 105 | " | " | F$_{19}$ | " | " |
| 106 | " | " | F$_{20}$ | " | " |
| 107 | " | " | F$_{21}$ | " | " |
| 108 | " | " | F$_{22}$ | " | " |
| 109 | " | " | F$_{23}$ | " | " |
| 110 | " | —H$_2$C—⌬— | F$_4$ | —CH$_3$ | " |
| 111 | " | " | F$_9$ | " | " |
| 112 | " | " | F$_{17}$ | " | " |
| 113 | " | —NH—CO—CH$_2$— | F$_4$ | " | " |
| 114 | " | " | F$_9$ | " | " |
| 115 | " | " | F$_{17}$ | " | " |
| 116 | " | —NH—CO—⌬—CH$_2$— | F$_4$ | " | " |
| 117 | " | " | F$_9$ | " | " |
| 118 | " | " | F$_{17}$ | " | " |
| 119 | " | —H$_2$C—⌬—NH—CO—CH$_2$— | F$_4$ | " | " |
| 120 | " | " | F$_9$ | " | " |
| 121 | " | " | F$_{17}$ | " | " |
| 122 | | | | | |
| 123 | " | —H$_2$C—⌬(Cl)—NH—CO—CH$_2$— | F$_4$ | " | " |
| 124 | " | " | F$_9$ | " | " |
| 125 | " | " | F$_{17}$ | " | " |
| 126 | | | | | |
| 127 | " | —H$_2$C—⌬(CH$_3$)—NH—CO—CH$_2$— | F$_4$ | " | " |
| 128 | " | " | F$_9$ | " | " |
| 129 | " | " | F$_{17}$ | " | " |
| 130 | " | —CH$_2$—CH(—)—CH$_3$ | F$_4$ | —⌬ | " |
| 131 | " | " | F$_9$ | " | " |
| 132 | " | " | F$_{17}$ | " | " |
| 133 | " | —NH—CO—CH$_2$— | F$_4$ | " | " |
| 134 | " | " | F$_9$ | " | " |
| 135 | " | " | F$_{17}$ | " | " |
| 136 | " | —NH—CO—⌬—CH$_2$— | F$_4$ | " | " |
| 137 | " | " | F$_9$ | " | " |
| 138 | " | " | F$_{17}$ | " | " |
| 139 | " | —H$_2$C—⌬— | F$_4$ | " | " |
| 140 | " | " | F$_9$ | " | " |
| 141 | " | " | F$_{17}$ | " | " |

The 17.25 parts of 1-amino-2-nitro-4-chlorobenzene used in Examples 8 and 13 can be replaced by the equivalent amount of one of the amines named below, on which dyes showing equally good properties are obtained. These dyes give dyeings of yellow to reddish yellow shade on polyacrylonitrile fibres.

1-amino-2-nitro-4-methylbenzene
1-amino-4-benzoylaminobenzene
1-amino-4'-chlorodiphenylether 1-amino-4-benzenesulfonic acid-N,N-dimethylamide
1-amino-2-chlorobenzene
1-amino-4-chlorobenzene
1-amino-3-chlorobenzene
1-amino-2,5-dichlorobenzene
1-amino-3,4-dichlorobenzene
1-amino-2-bromobenzene
1-amino-3-bromobenzene
1-amino-2,4,6-tribromobenzene
1-amino-2,4,6-trichlorobenzene
1-amino-2-methoxybenzene
1-amino-2-methylbenzene
1-amino-3-methylbenzene
1-amino-4-methylbenzene
1-amino-2,5-dimethylbenzene
1-amino-2-methoxybenzene-5-sulphonamide
1-amino-4-nitrobenzene
1-amino-3-nitrobenzene
1-aminobenzene
1-amino-2-methoxy-4-nitrobenzene
1-amino-2-methoxy-5-nitrobenzene
1-amino-3-chloro-4-methoxybenzene
1-amino-4-acetylaminobenzene
1-amino-4-methoxybenzene
1-amino-4-ethoxybenzene
1-amino-2,6-dichloro-4-nitrobenzene
1-amino-2,4,5-trichlorobenzene
4-amino-4-chlorodiphenylether.

EXAMPLE 142

10.7 Parts of 1-amino-4-methylbenzene are diazotized with 6.9 parts of sodium nitrite in 200 parts of 6% hydrochloric acid at 0°. To the ice-cold azo solution is added over one hour a solution of 23 parts of 1-[pyridyl-(2)]-2-keto-3-cyano-4-methyl-6-hydroxy-1,2-dihydropyridine, 30 parts of dimethylformamide and 70 parts of methyl alcohol. The reaction mixture is adjusted to pH 4.0 with sodium acetate and stirred until the coupling reaction has run its course. The dye settles out and is filtered off, washed with water and dried. 10 Parts of the dye are reacted with 100 parts of dimethyl sulphate for one hour at 100°. The solution is subsequently diluted with 300 parts of ethyl alcohol and the quaternized dye precipitated by the addition of an ether. After filtration, drying and grinding it is obtained as a water soluble powder which gives very fast yellow dyeings on polyacrylonitrile fibres.

A similar equally valuable dye is obtained when the 10.7 parts of 1-amino-4-methylbenzene used are replaced by 13.5 parts of 1-amino-4-acetylbenzene and the procedure of this Example is followed in all other respects.

The coupling component used is prepared by condensation of the reaction product of cyanoacetic acid ethyl ester and 2-aminopyridine with acetoacetic acid ethyl ester in the presence of a secondary amine, e.g., morpholine.

EXAMPLE 143

19.7 Parts of 4-amino-1,1'-azobenzene, after diazotization in the known way with 6.9 parts of sodium nitrite in 200 parts of 6% hydrochloric acid, are added to a solution of 21.5 parts of 1-(2'-hydroxyethyl)-2-keto-3-cyano-4-methyl-6-hydroxy-1,2-dihydropyridine and 120 parts of methyl alcohol. The reaction mixture is adjusted to pH 4.0 with sodium carbonate and stirred further until the coupling reaction is complete. 20.1 Parts of the dye so formed are dissolved in 180 parts of dimethylformamide. At room temperature 5.6 parts of thionyl chloride are added to the solution, which is then stirred for 45 minutes at 60°. The chlorinated dye is precipitated by dilution with water, collected on a filter, washed with water and dried. 21 Parts of this dye are added to 200 parts of dimethylformamide and 7.1 parts of pyridine and the solution is maintained at 70° for one hour. The thus obtained dye dyes polyacrylonitrile fibres in fast reddish yellow shades.

In place of pyridine the chlorinated dye may be treated with the equivalent amount of asymmetrical dimethylhydrazine, N-methylpyrrolidine or trimethylamine to obtain the corresponding quaternary salts.

The coupling component may be prepared by condensation of cyanoacetic acid 2-hydroxyethylamine with acetoacetic acid ester, for example in the presence of a secondary amine such as diethylamine, morpholine, diethanolamine or piperidine.

EXAMPLE 144

22.1 Parts of 4-aminobenzoic acid-3'-dimethylamino-n-propylamide are dissolved in a mixture of 40 parts of 30% hydrochloric acid and 200 parts of water and diazotized at 0° with 6.9 parts of sodium nitrite. A solution of 18 parts of 1-methyl-2-keto-3-cyano-4-methyl-6-hydroxy-1,2-dihydropyridine and 120 parts of methyl alcohol is added dropwise to the ice-cold diazo solution. The pH of the reaction solution is then adjusted to 4.5 with sodium hydroxide and it is stirred continuously at 10° until the coupling reaction has run its course. The dye formed is isolated in the normal way and dried. 15 Parts of this dye are dissolved in 300 parts of chloroform in the presence of 15 parts of dimethyl sulphate and the solution is boiled for several hours with reflux. On cooling the quaternized dye in the form of the methyl sulphate is collected on a filter and dried. After purification by recrystallization it is soluble in water. It is applicable to polyacrylonitrile and polyvinylidene fibres, on which it gives greenish yellow dyeings of good light and wet fastness.

If 15 parts of the aforedescribed, unquaternized dye are mixed with 300 parts of chloroform and 30 parts of dimethylformamide and reacted with chloramine at room temperature, the N',N'-dimethylhydrazinium chloride is obtained, which likewise is soluble in water. This dye gives intense greenish yellow shades of high light and wet fastness on polyacrylonitrile fibres.

The N',N'-dimethylhydrazinium salt employed for the aforestated dye can be prepared by dissolving 15 parts of the starting dye in 500 parts of water at 45° and reacting with hydroxylamine-O-sulphonic acid.

EXAMPLE 145

9.3 Parts of 1-aminobenzene are dissolved in 200 parts of 6% hydrochloric acid at 0° and diazotized with 6.9 parts of sodium nitrite. To the ice-cold diazo solution is added over one hour an aqueous solution of 24 parts of 1-piperidyl-(4)-2-keto-3-cyano-4-methyl-6-hydroxy-1,2-dihydropyridine and 200 parts of water. The pH of the reaction solution is then adjusted to 5.5 by dropping in 10% sodium carbonate solution and it is stirred further at 0° until coupling is complete. The solution is then adjusted to a mineral acid reaction with hydrochloric acid and at 45° sodium chloride is added for precipitation. The dye settles out as the hydrochloride and is filtered off, washed with hydrochloric acid brine, dried and ground. It is obtained as a water-soluble yellow powder which gives very fast yellow dyeings on polyacrylonitrile.

For conversion into the quanternary compound 10 parts of the dye are dissolved in 200 parts of chlorobenzene. 15 Parts of dimethyl sulphate and 1.2 parts of magnesium oxide are added and the reaction is conducted for several hours at 130°. On cooling to room temperature the quaternized dye is precipitated with acetone, filtered off and washed with acetone. The dye can be precipitated from aqueous hydrochloric acid solution with sodium chloride in the form of the chloride.

In this form also it is suitable for producing very fast yellow shades on polyacrylonitrile fibres.

The coupling component employed in this Example can be prepared by condensing the reaction product of cyanoacetic acid methyl ester and 4-aminopiperidine with acetoacetic acid methyl ester.

EXAMPLE 146

99 Parts of cyanoacetic acid methyl ester are added dropwise to 102 parts of 3-aminodimethylpropylamine so that the reaction temperature does not increase to above 40°. The mixture is then boiled with reflux, after which the temperature is allowed to decrease slightly and 116 parts of acetoacetic acid methyl ester and 7.1 parts of diethylamine are added. Boiling is continued for 3 hours with reflux. Then the methyl alcohol and the water of the reaction mixture are distilled off at reduced pressure. After cooling to 95° the residue in the reaction vessel is diluted with 100 parts of water to a 52.5% aqueous solution of 1-(3'-dimethylaminopropyl)-propyl-2-keto-3-cyano-4-methyl-6-hydroxy-1,2-dihydropyridine. 50 Parts of this solution are dropped into an ice-cold aqueous diazo suspension prepared by the normal method with 24.8 parts of 1-aminobenzene-4-sulphonic acid phenylamide. The dye is isolated as the hydrochloride. On drying and grounding it is obtained as a water soluble yellow powder which dyes polyacrylonitrile and polyvinylidene fibres in very fast greenish yellow shades.

15 Parts of the dye thus obtained are entered into 100 parts of dimethyl sulphate and reacted for one hour at 100°. After subsequent dilution with 300 parts of methyl alcohol the quaternated dye is precipitated by the addition of ether and dried. It is a dye salt which dissolved in water with a yellow colour and dyes polyacrylonitrile and polyvinylidene fibres in greenish yellow shades of very good fastness.

Quaternized dyes of comparably high quality can be prepared by replacing the 102 parts of 3-aminodimethylpropylamine employed and produced as in the foregoing Example by the equivalent amount of one of the following amines and quaternized according to the details given in the Example.
2-dimethylaminoethylamine,
2-diethylaminoethylamine,
2-di-isopropylaminoethylamine,
3-diethylaminopropylamine-(1),
3-dibutylaminopropylamine,
2-dipropylaminoethylamine,
2-dibutylaminoethylamine,
4-dimethylaminobutylamine-(1),
4-diethylaminobutylamine-(3),
2-dimethylamino-tert.butylamine,
1,3-bis-(dimethylamino)-2-aminopropane,
1,3-bis-piperidino-2-aminopropane,
N-(2-aminoethyl)-N'-(methyl)-piperazine,
N-(2-aminoethyl)-piperazine,
N-(2-aminoethylmorpholine),
N-(3-aminopropyl)-morpholine,
4-dimethylaminobenzylamine,
4-diethylaminophenylethylamine,
4-amino-N,N-dimethylbenzylamine,
1-amino-3-diethylaminopropanol,
N-(2-hydroxyethyl)-ethylenediamine,
3-(2-dimethylaminoethoxy)-propylamine,
3-(2-dimethylaminoethylamino)-propylamine,
2-dihydroxyethylaminoethylamine,
2-dichloroethylaminoethylamine,
2'-aminoethylpyridine,
1-amino-4-methylpiperazine,
3-dihydroxyethylaminopropylamine,
1-(2'-aminoethylamino)-2-propanol,
2-(2'-aminoethyl)-1-methylpyrrolidine, Similar quaternized dyes of equally good quality can be produced by replacing the 24.8 parts of 1-aminobenzene-4-sulphonic acid phenylamide used in the preceding Example by the equivalent amount of one of the following:
4-aminobenzoic acid ethylester,
4-aminobenzoic acid phenylamide,
2-aminobenzoic acid methylester,
1-amino-2-nitro-4-methylbenzene,
1-amino-2,5-dichlorobenzene,
4-aminodiphenyl,
2-aminodiphenyl,
2-amino-4-chlorodiphenylether,
4-amino-4'-chlorodiphenylether,
1-amino-4-methylbenzene-3-sulphonic acid phenylamide,
2-amino-benzene-1-sulphonic acid N-ethyl-N-phenylamide,
1-amino-3-benzoylaminobenzene,
1-amino-3-chloro-4-methoxybenzene,
4-amino-2',4'-dinitrodiphenylamine,
1-amino-4-methylbenzene,
1-amino-2-methyl-4-chlorobenzene,
1-amino-2-chlorobenzene,
1-amino-2-cyano-4-chlorobenzene,
1-amino-2-chloro-4-nitrobenzene,
1-amino-2-methoxy-4-nitrobenzene,
1-amino-4-benzoylaminobenzene,
4-aminobenzenesulphonic acid dimethylamide,
1-amino-2-methyl-5-nitrobenzene,
1-amino-4-carbethoxybenzene,
4-amino-azobenzene,
4-amino-4'-methylbenzophenone.

EXAMPLE 147

25.6 Parts of 4-amino-4'-chlorodiphenylether-hydrochloride are dissolved in 300 parts of water and after the addition of 18 parts of 30% hydrochloric acid are diazotized by the normal method with 6.9 parts of sodium nitrite. The diazo solution is added to a solution of 24.7 parts of 1-(3'-N',N'-dimethylaminopropyl)-2-keto-3-cyano-4-methyl-6-hydroxy-1,2-dihydropyridine and 200 parts of 2% aqueous hydrochloric acid at 10°, with continuous stirring to the end-point of the coupling reaction. The dye formed is salted out at 50° with sodium chloride, filtered off and dried. This new dye is an orange powder which gives bright reddish yellow shades of high light and wet fastness on polyacrylonitrile fibres.

15 Parts of the dye are stirred into 150 parts of isopropyl alcohol and after the addition of 15 parts of dimethyl sulphate the mixture is reacted for one hour with heating. On cooling the quaternized dye is precipitated with an ether, dioxane or acetone, filtered off and dried. Applied from aqueous solution, it gives reddish yellow dyeings on polyacrylonitrile and polyvinylidene fibres which are fast to light and wet treatments.

The coupling component is prepared by condensation of cyanoacetic acid-3-dimethylamino-n-propylamide with acetoacetic acid ethyl ester.

EXAMPLE 148

12.75 Parts of 1-amino-2-chlorobenzene are dissolved in a mixture of 250 parts of water and 40 parts of 30% hydrochloric acid and coupled in the normal way with 6.9 parts of sodium nitrite at 0° C. In the course of one hour a solution of 1-(4'-(2''-hydroxyethyl)-phenyl-2-keto-3-cyano-4-methyl-6-hydroxy-1,2-dihydropyridine in 150 parts of glacial acetic acid is added to the diazo solution with stirring and cooling. Stirring is continued until the coupling reaction is complete. The dye settles out in crystalline form and is filtered off and purified by recrystallization. 40.8 Parts of the dye are dissolved in 300 parts of pyridine, 22 parts of 4-methylbenzene-sulphonic acid chloride are added at 10° and the reaction solution is stirred for 7 hours at 10°. The esterified dye is precipitated by dilution with 1500 parts of water, filtered off and dried. 11.3 Parts of the dried dye are added to a mixture of 100 parts of toluene, 2 parts of dimethylaminobenzene and 3.6 parts of N,N-dimethylhydrazine and the mixture is reacted at the boil for 8 hours with reflux. The quaternized dye settles out and on cooling it is collected on a filter, washed with chloroform and dried. It dyes polyacrylonitrile and polyvinylidene fibres in greenish yellow shades which have excellent fastness properties.

Similar dyes also of yellow hue are obtained when pyridine, trimethylamine, triethylamine, N-methylpyrrolidine or N-methylmorpholine is employed in place of N,N-dimethylhydrazine.

The coupling component used in this Example can be prepared by condensation of cyanoacetic acid-4-(2'-hydroxyethyl)phenylamide with acetoacetic acid ethyl ester in the presence of a secondary amine, e.g., pyridine. The following Examples may be produced as indicated in one of Examples 1 to 148 and/or are the formulae of representative dyes of the said foregoing Examples:

EXAMPLE 149

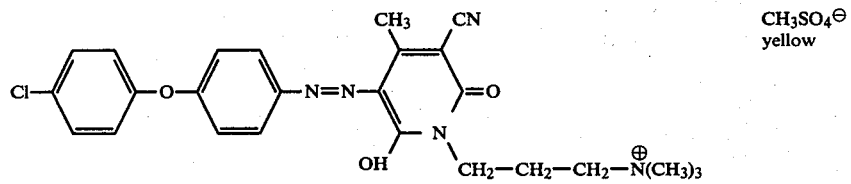

EXAMPLE 150

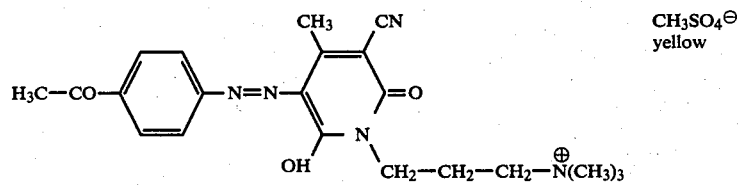

EXAMPLE 151

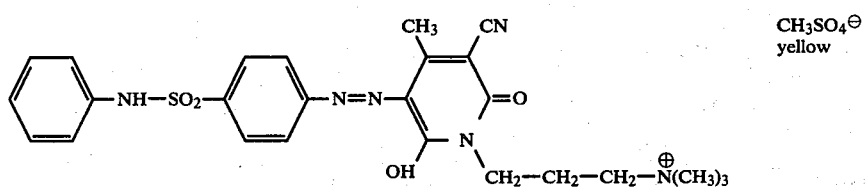

EXAMPLE 152

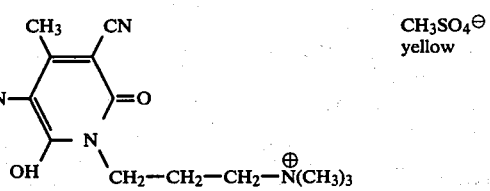

EXAMPLE 153

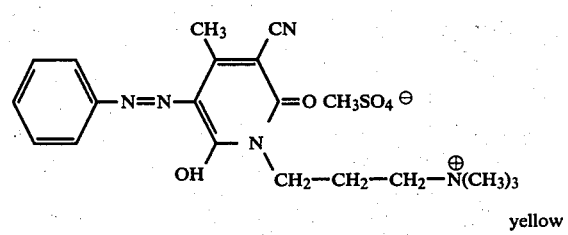

EXAMPLE 154

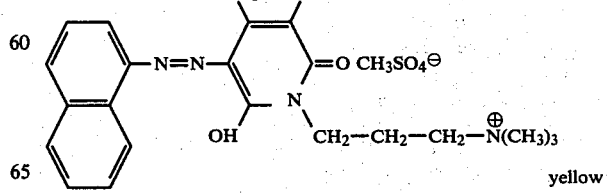

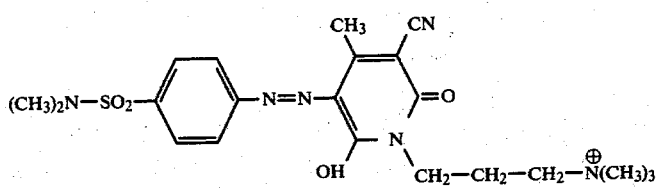
EXAMPLE 155
CH$_3$SO$_4^\ominus$
yellow
EXAMPLE 158
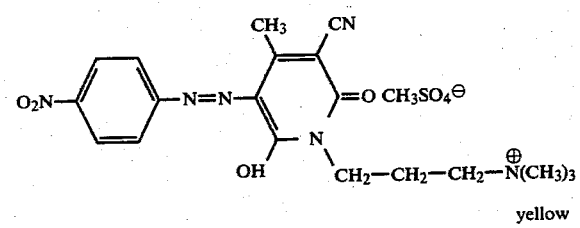
EXAMPLE 156
yellow
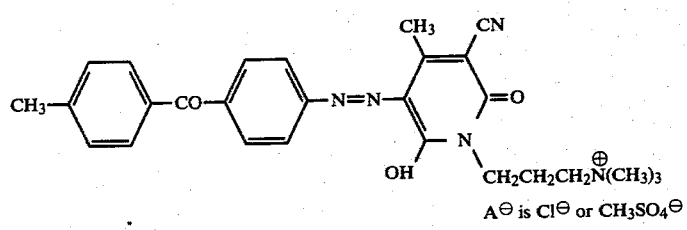
A$^\ominus$ is Cl$^\ominus$ or CH$_3$SO$_4^\ominus$
EXAMPLE 157
A$^\ominus$
yellow
EXAMPLE 159
yellow
A$^\ominus$ is Cl$^\ominus$ or CH$_3$SO$_4^\ominus$
EXAMPLE 160
yellow
A$^\ominus$ is Cl$^\ominus$ or CH$_3$SO$_4^\ominus$

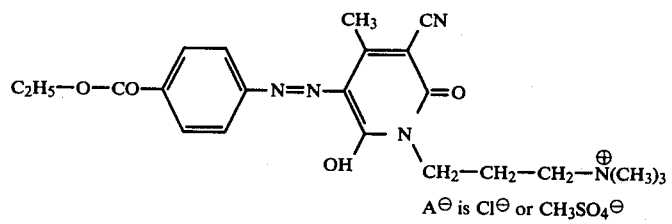

$A^\ominus$ is $Cl^\ominus$ or $CH_3SO_4^\ominus$

EXAMPLE 161

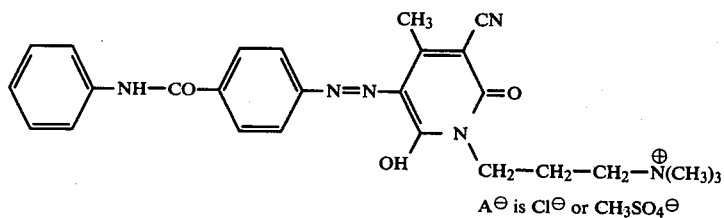

$A^\ominus$ is $Cl^\ominus$ or $CH_3SO_4^\ominus$

EXAMPLE 162

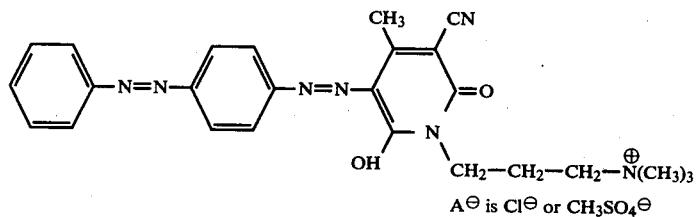

$A^\ominus$ is $Cl^\ominus$ or $CH_3SO_4^\ominus$

EXAMPLE 163

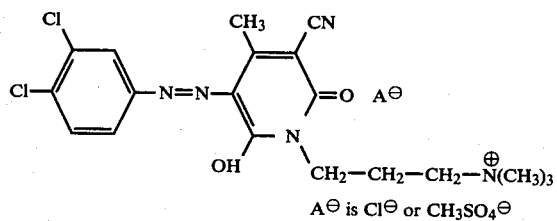

$A^\ominus$ is $Cl^\ominus$ or $CH_3SO_4^\ominus$ yellow $A^\ominus$
yellow

EXAMPLE 164

$A^\ominus$
yellow $A^\ominus$
golden yellow

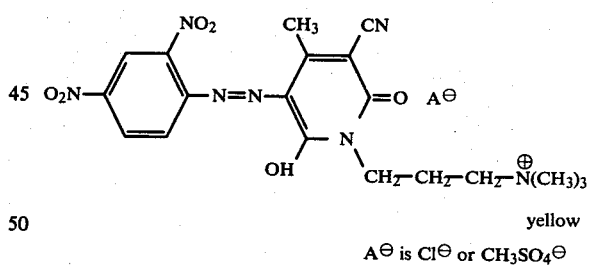

$A^\ominus$ is $Cl^\ominus$ or $CH_3SO_4^\ominus$ yellow

EXAMPLE 165

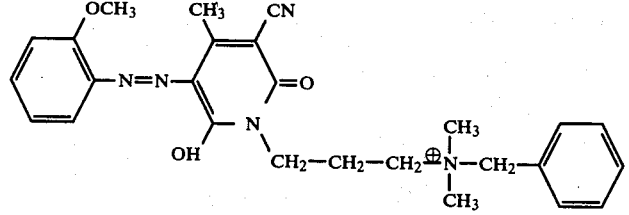

$Cl^\ominus$
yellow

EXAMPLE 166
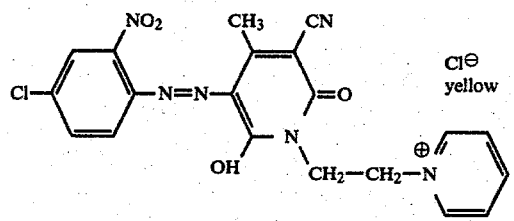
yellow
EXAMPLE 167
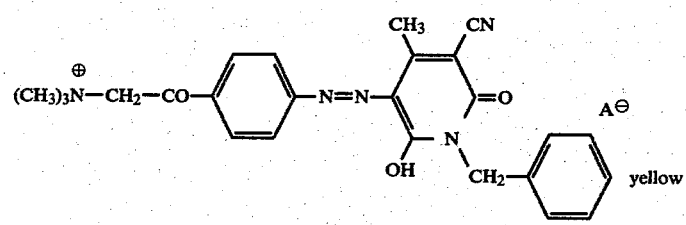
$A^\ominus$ is $Cl^\ominus$ or $CH_3SO_4^\ominus$
yellow
EXAMPLE 168
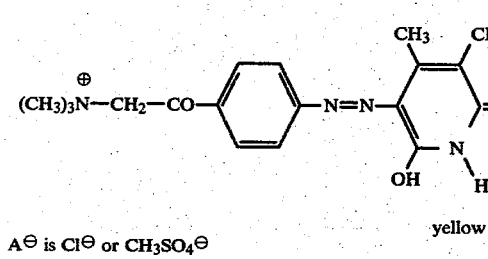
$A^\ominus$ is $Cl^\ominus$ or $CH_3SO_4^\ominus$
yellow
EXAMPLE 169
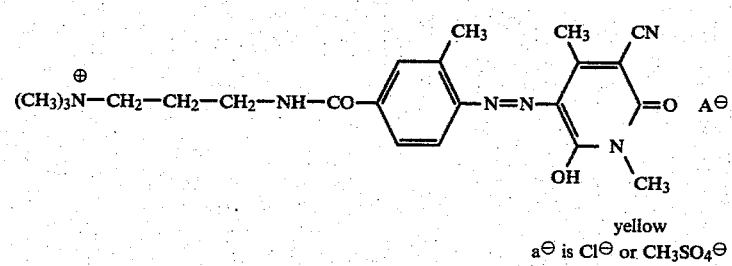
yellow
$a^\ominus$ is $Cl^\ominus$ or $CH_3SO_4^\ominus$
EXAMPLE 170
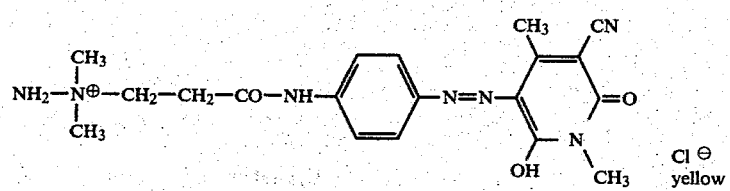
yellow
EXAMPLE 171
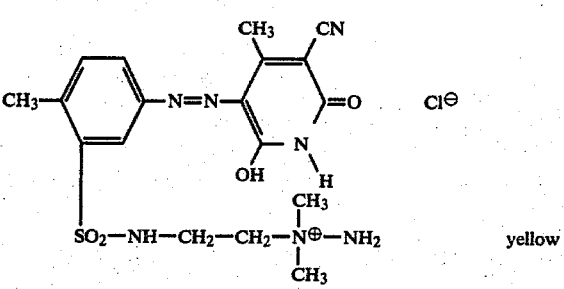
yellow
EXAMPLE 172
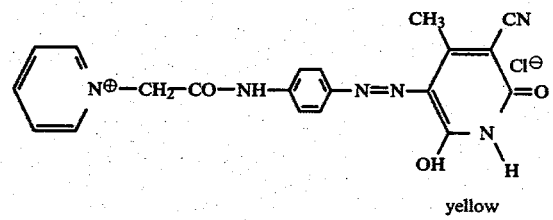
yellow
What we claim is:
1. A compound of the formula

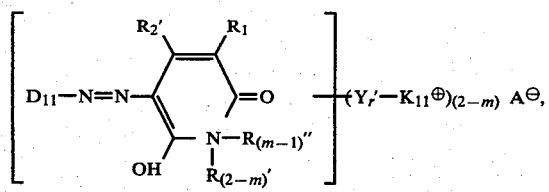

wherein
$D_{11}$ is phenyl, naphthyl, tetrahydronaphthyl, pyridyl, quinolyl, tetrahydroquinolyl, 1,2,4-triazolonyl, 1,2,4-triazolyl, indazolyl, 1,3,4-thiadiazolyl, thiazolyl or benzothiazolyl, or a substituted derivative thereof, wherein each substituent is independently halo, nitro, cyano, thiocyano, hydroxy, alkyl, alkoxy, trifluoroalkyl, trichloroalkyl, phenyl, phenoxy, chlorophenoxy, amino, alkylamino, dialkylamino, anilino, 2,4-dinitroanilino, phenylcarbamoyl, alkylsulfonyl, arylsulfonyl, sulfamoyl, alkylsulfamoyl, dialkylsulfamoyl, arylsulfamoyl, N-alkyl-N-phenylsulfamoyl, alkylcarbonyl, alkoxycarbonyl, alkylcarbonylamino, benzamido, benzoyl, alkylbenzoyl, phenylazo, diphenylazo or naphthylazo,
$R_1$ is hydrogen or cyano,
$R_2'$ is alkyl, carbocyclic aryl, benzyl or heterocyclyl,
$R'$ is hydrogen, alkyl, substituted alkyl, alkoxyalkyl, cyclohexyl, carbocyclic aryl, substituted carbocyclic aryl, heterocyclyl, substituted heterocyclyl, amino or substituted amino,
$R''$ is

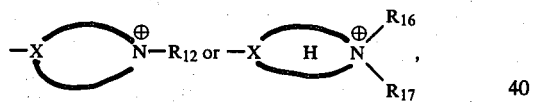

$Y'$ is —Alk—, —Z—Alk—, —Alk—Z—, —Alk'—Z—Alk'—, —CO—, —SO$_2$— or

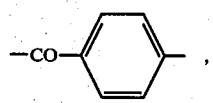

wherein Alk is straight or branched chain alkylene of 1 to 12 carbon atoms or straight or branched chain alkylene of 1 to 12 carbon atoms substituted by hydroxy, each Alk' is independently straight or branched chain alkylene, with the proviso that the two Alk' radicals together contain 2 to 12 carbon atoms, and

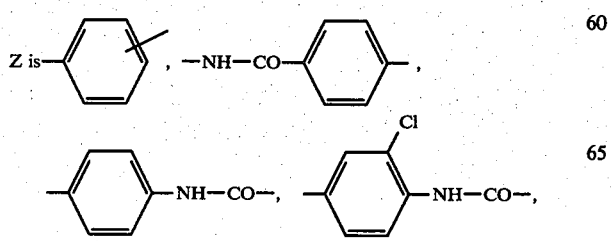

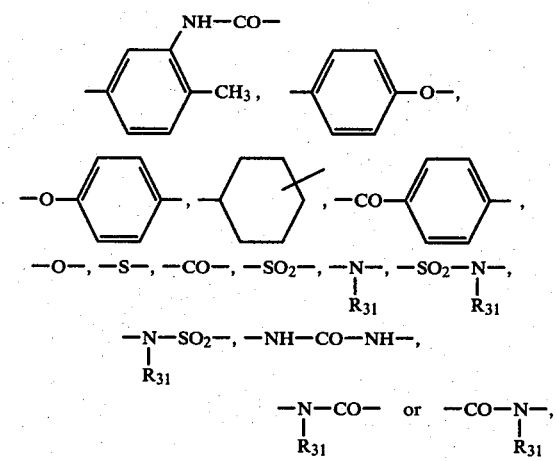

wherein $R_{31}$ is hydrogen or alkyl,

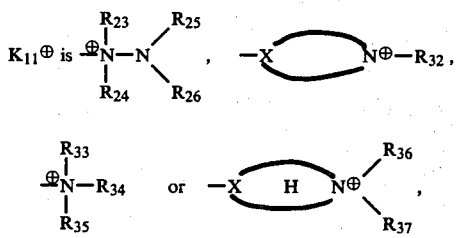

m is 1 or 2,
r is 0 or 1, and
$A^{\ominus}$ is an anion,
wherein $R_{12}$ is hydrocarbyl or substituted hydrocarbyl,
$R_{16}$ is hydrocarbyl or substituted hydrocarbyl,
$R_{17}$ is hydrocarbyl, substituted hydrocarbyl, amino or substituted amino,
each of $R_{23}$ and $R_{24}$ is independently alkyl, substituted alkyl, cycloalkyl or substituted cycloalkyl, or $R_{23}$ and $R_{24}$ taken together and with the nitrogen to which they are joined form a pyrrolidinium, piperazinium, morpholinium, aziridinium or piperidinium ring,
each of $R_{25}$ and $R_{26}$ is independently hydrogen, alkyl, substituted alkyl, cycloalkyl or substituted cycloalkyl,
each of $R_{32}$, $R_{33}$, $R_{34}$ and $R_{36}$ is independently alkyl, substituted alkyl, carbocyclic aryl or substituted carbocyclic aryl,
$R_{35}$ is alkyl, substituted alkyl, cycloalkyl or substituted cycloalkyl, and
$R_{37}$ is amino, substituted amino, alkyl, substituted alkyl, cycloalkyl, substituted cycloalkyl, carbocyclic aryl or substituted carbocyclic aryl, or
$R_{23}$ and $R_{25}$ taken together and with the nitrogens to which they are joined form a pyrazolidinium, pyridazinium or pyrazolinium ring, or
$R_{23}$, $R_{24}$, $R_{25}$ and $R_{26}$ taken together and with the nitrogens to which they are joined form a

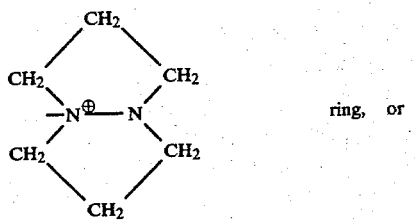 ring, or $R_{33}$ and $R_{34}$ taken together and with the nitrogen to which they are joined form a pyrrolidinium, piperidinium, morpholinium, aziridinium or piperazinium ring, or $R_{33}$, $R_{34}$ and $R_{35}$ taken together and with the nitrogen to which they are joined are

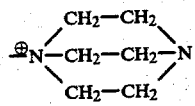

or a pyridinium or quinolinium ring,

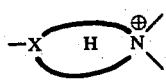

is a piperidinium, pyrrolidinium, morpholinium, aziridinium, piperazinium or pyrazolinium ring,

is a pyridinium, quinolinium, isoquinolinium, tetrahydroquinolinium, pyrazolium, triazolium, pyridazinium, imidazolium, pyrimidinium, thiazolium, benzothiazolium, thiadiazolium, indazolium, pyrrolium, indolium, oxazolium, isoxazolium or tetrazolium ring, and X is a carbon or nitrogen atom, wherein each hydrocarbyl is independently alkyl, cycloalkyl or carbocyclic aryl, each substituent of substituted alkyl is independently halo, hydroxy, cyano or phenyl, each substituent of substituted cycloalkyl is independently halo, hydroxy, cyano, phenyl or alkyl, each substituent of substituted carbocyclic aryl and substituted heterocyclyl is independently halo, nitro, cyano, thiocyano, hydroxy, alkyl, alkoxy, trifluoroalkyl, trichloroalkyl, phenyl, phenoxy, amino, alkylamino, dialkylamino, anilino, alkylsulfonyl, carbocyclic arylsulfonyl, sulfamoyl, alkylsulfamoyl, dialkylsulfamoyl, carbocyclic arylsulfamoyl, phenylazo, diphenylazo or naphthylazo, each substituent of substituted amino is independently alkyl, cycloalkyl, carbocyclic aryl or carbocyclic arylalkyl, each carbocyclic aryl is independently phenyl, naphthyl or tetrahydronaphthyl, each heterocyclyl is independently pyridyl, quinolyl, tetrahydroquinolyl, piperidyl, pyrrolidinyl, morpholinyl, aziridinyl, piperazinyl, isoquinolyl, pyrazolinyl, triazolyl, triazolonyl, pyridazinyl, imidazolyl, pyrimidinyl, thiazolyl, benzothiazolyl, indazolyl, pyrrolyl, indolyl, oxazolyl, isoxazolyl, pyrazolidinyl, trimethylenepyrazolidinyl, thienyl or tetrazolyl, each alkyl, cycloalkyl, alkyl radical or each alkoxyalkyl, trifluoroalkyl, trichloroalkyl, alkylamino, dialkylamino, alkylcarbonyl, alkylbenzoyl, arylalkyl, alkylcarbonylamino, alkylsulfonyl, alkylsulfamoyl, dialkylsulfamoyl, N-alkyl-N-phenylsulfamoyl, alkyl chain of substituted alkyl and cycloalkyl ring of substituted cycloalkyl independently has not more than 12 carbon atoms, each alkoxy and alkoxy radical of alkoxycarbonyl and alkoxyalkyl independently has 1 to 6 carbon atoms, and each halo is independently chloro, bromo or fluoro.

2. A compound according to claim 1 having the formula

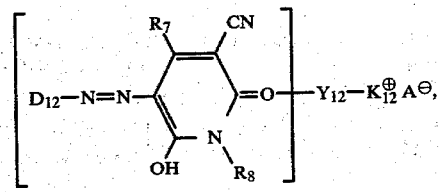

wherein $D_{12}$ is phenyl, substituted phenyl having 1 to 3 substituents or naphthyl, wherein each substituent of substituted phenyl is independently chloro, bromo, nitro, cyano, alkyl, alkoxy, phenyl, phenoxy, 4-chlorophenoxy, 2,4-dinitroanilino, alkylcarbonyl, benzoyl, alkylbenzoyl, alkoxycarbonyl, phenylcarbamoyl, alkylcarbonylamino, benzamido, sulfamoyl, alkylsulfamoyl, dialkylsulfamoyl, N-alkyl-N-phenylsulfamoyl, phenylsulfamoyl or phenylazo, $R_7$ is alkyl, benzyl or phenyl, $R_8$ is hydrogen or alkyl, $Y_{12}$ is

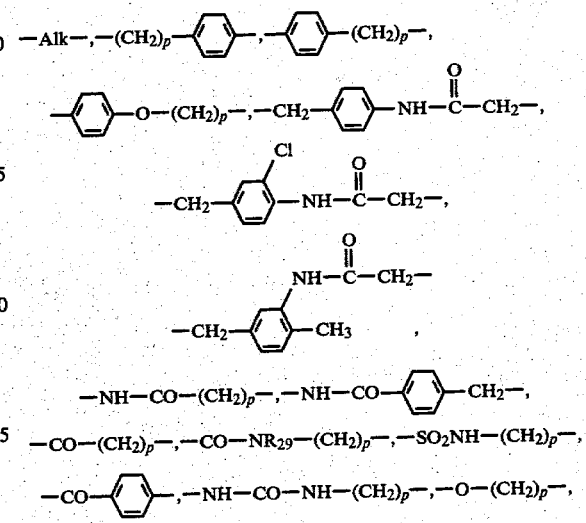

-continued

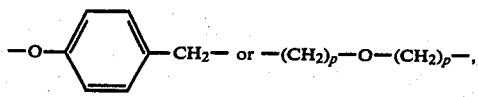

wherein Alk is straight or branched chain alkylene of 1 to 6 carbon atoms, each p is independently 1 to 6 and $R_{29}$ is hydrogen or alkyl, $K_{12}^\oplus$ is

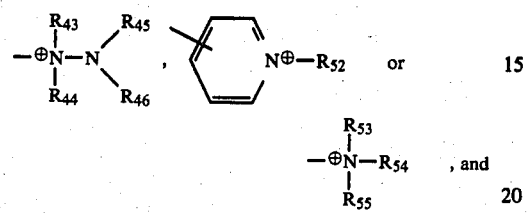

$A^\ominus$ is an anion, wherein each of $R_{43}$ and $R_{44}$ is alkyl, 2-hydroxyethyl or 2-cyanoethyl, or $R_{43}$ and $R_{44}$ taken together and with the nitrogen to which they are joined are pyrrolidinium, piperidinium or morpholinium, each of $R_{45}$ and $R_{46}$ is independently hydrogen or alkyl, each of $R_{52}$, $R_{53}$ and $R_{54}$ is independently alkyl, $R_{55}$ is alkyl or benzyl, or $R_{53}$ and $R_{54}$ taken together and with the nitrogen to which they are joined are pyrrolidinium, piperidinium or morpholinium, or $R_{53}$, $R_{54}$ and $R_{55}$ taken together and with the nitrogen to which they are joined are pyridinium, methylpyridinium or quinolinium, each alkyl and alkyl group of each alkylcarbonyl, alkylbenzoyl, alkylcarbonylamino, alkylsulfamoyl, dialkylsulfamoyl and N-alkyl-N-phenylsulfamoyl independently has 1 to 4 carbon atoms, and each alkoxy and alkoxy group of each alkoxycarbonyl independently has 1 to 3 carbon atoms.

3. A compound according to claim 1 having the formula

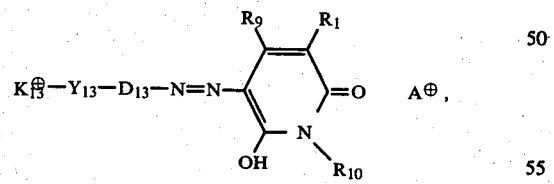

wherein $D_{13}$ is phenylene or substituted phenylene, wherein each substituent of substituted phenylene is independently chloro, bromo, nitro, methyl, ethyl, methoxy, ethoxy or phenoxy, $R_1$ is hydrogen or cyano, $R_9$ is alkyl or phenyl, $R_{10}$ is hydrogen, alkyl, monosubstituted alkyl, cyclohexyl or phenyl, wherein the substituent of monosubstituted alkyl is alkoxy, hydroxy or phenyl, $Y_{13}$ is

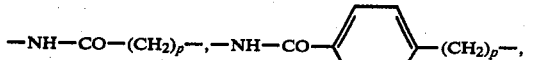
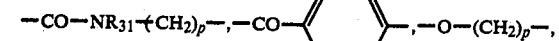
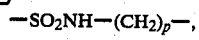

wherein p is 1 to 6, $K_{13}^\oplus$ is

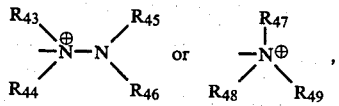

each of $R_{43}$ and $R_{44}$ is independently alkyl, each of $R_{45}$ and $R_{46}$ is independently hydrogen or alkyl, each of $R_{47}$ and $R_{48}$ is independently alkyl or hydroxyalkyl, and $R_{49}$ is alkyl, or $R_{47}$ and $R_{48}$ taken together and with the nitrogen to which they are joined are pyrrolidinium, or $R_{47}$, $R_{48}$ and $R_{49}$ taken together and with the nitrogen to which they are joined are pyridinium or quinolinium, wherein each alkyl, hydroxyalkyl and alkyl chain of monosubstituted alkyl independently has 1 to 4 carbon atoms, and alkoxy has 1 to 3 carbon atoms.

4. A compound according to claim 3 wherein $D_{13}$ is phenylene or substituted phenylene, wherein substituted phenylene has 1 or 2 substituents and each substituent of substituted phenylene is independently chloro, bromo, nitro, methyl, ethyl, methoxy, ethoxy or phenoxy, $R_1$ is cyano, $R_9$ is methyl, $R_{10}$ is hydrogen, alkyl, monosubstituted alkyl, cyclohexyl or phenyl, wherein the substituent of monosubstituted alkyl is methoxy, hydroxy or phenyl, $Y_{13}$ is

—NH—CO—CH$_2$—, —NH—CO—CH$_2$CH$_2$—,

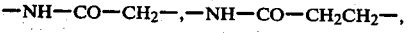

—NH—CO—NH—CH$_2$CH$_2$—,

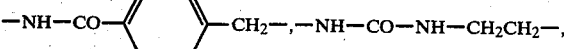

—CO—CH$_2$—, —CO—CH$_2$CH$_2$—, —CO—NH—CH$_2$CH$_2$—,

—CO—NH—CH$_2$CH$_2$CH$_2$—, —CO—N(CH$_3$)—CH$_2$CH$_2$—,

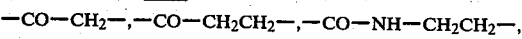

, —O—CH$_2$CH$_2$—,

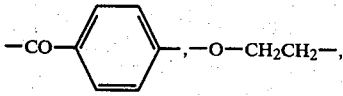

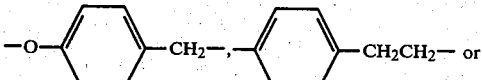

-continued $-SO_2-NH-CH_2CH_2-$, and $K_{13}^{\oplus}$ is $$\overset{R_{47}}{\underset{R_{48}}{\oplus N}}-\overset{CH_3}{\underset{CH_3}{}} \quad \text{or} \quad -\overset{CH_3}{\underset{CH_3}{\oplus N}}-\overset{H}{\underset{H}{N}}$$

5. A compound according to claim 3 wherein $D_{13}$ is phenylene or monosubstituted phenylene, wherein the substituent of monosubstituted phenylene is chloro, bromo, methyl, ethyl, methoxy, ethoxy or phenoxy, $R_9$ is methyl, $R_{10}$ is methyl, ethyl, phenyl or cyclohexyl, and $Y_{13}$-$K_{13}^{\oplus}$ is $-CO-NH-CH_2CH_2-\overset{\oplus}{N}(CH_3)_3$, $-CO-NCH_3-CH_2CH_2-\overset{\oplus}{N}(CH_3)_3$, $-CO-CH_2-\overset{CH_2CH_2OH}{\underset{CH_2CH_2OH}{\overset{\oplus}{N}}}-CH_3$, $-CO-CH_2CH_2-\overset{CH_2CH_2OH}{\underset{CH_3}{\overset{\oplus}{N}}}-CH_3$, $-CO-\phantom{x}\!\!\!\!\!\!\!\bigcirc\!\!\!\!\!\!\!\!\phantom{x}-\overset{\oplus}{N}(CH_3)_3$, $-NH-CO-\phantom{x}\!\!\!\!\!\!\!\bigcirc\!\!\!\!\!\!\!\!\phantom{x}-CH_2-\overset{\oplus}{N}(CH_3)_3$, $-NH-CO-NH-CH_2CH_2-\overset{\oplus}{N}(CH_3)_3$, $-NH-CO-CH_2CH_2-\overset{\oplus}{N}(CH_3)_3$, $-O-CH_2CH_2-\overset{\oplus}{N}(CH_3)_3$ or $-O-\phantom{x}\!\!\!\!\!\!\!\bigcirc\!\!\!\!\!\!\!\!\phantom{x}-CH_2-\overset{\oplus}{N}(CH_3)_3$.

6. A compound according to claim 1 having the formula $$D_{11}-N=N-\underset{OH}{\overset{R_2'}{\underset{\phantom{x}}{\bigcirc}}}\!\!\!\!\!\!\!\!\overset{CN}{\underset{Y'-K_{11}^{\oplus}}{\overset{=O}{N}}} \quad A^{\ominus},$$

wherein $R_2'$ is alkyl of 1 to 4 carbon atoms or phenyl.

7. A compound according to claim 6 having the formula $$D_{14}-N=N-\underset{OH}{\overset{R_2'}{\underset{\phantom{x}}{\bigcirc}}}\!\!\!\!\!\!\!\!\overset{CN}{\underset{Y_{14}-K_{14}^{\oplus}}{\overset{=O}{N}}} \quad A^{\ominus},$$

wherein $D_{14}$ is phenyl, substituted phenyl or naphthyl, wherein substituted phenyl has 1 to 3 substituents and each substituent is independently chloro, bromo, nitro, cyano, alkyl, alkoxy, phenyl, phenoxy, 4-chlorophenoxy, alkylcarbonylamino, benzamido, alkylcarbonyl, benzoyl, alkylbenzoyl, alkoxycarbonyl, sulfamoyl, dialkylsulfamoyl, phenylsulfamoyl, N-alkyl-N-phenylsulfamoyl, phenylcarbamoyl, 2,4-dinitroanilino or phenylazo, $R_2'$ is alkyl or phenyl, $Y_{14}$ is $-(CH_2)_s-$, $-(CH_2)_t\!\!\!\!\!\bigcirc\!\!\!\!\!-$, $-NH-CO-CH_2-$, $-CH_2CH_2CH_2-O-CH_2CH_2-$, $-NH-CO-\!\!\!\!\!\bigcirc\!\!\!\!\!-CH_2-$, $-CH_2-\!\!\!\!\!\bigcirc\!\!\!\!\!-NH-CO-CH_2-$, $-CH_2-\!\!\!\!\!\overset{Cl}{\bigcirc}\!\!\!\!\!-NH-CO-CH_2-$, $-CH_2-\!\!\!\!\!\overset{NH-CO-CH_2-}{\underset{CH_3}{\bigcirc}}$, $-CH_2-\overset{CH_3}{\underset{\phantom{x}}{CH}}-$, $-\!\!\!\!\!\bigcirc\!\!\!\!\!-NH-CO-CH_2-$, $-\!\!\!\!\!\bigcirc\!\!\!\!\!-(CH_2)_s-$ or $-\!\!\!\!\!\bigcirc\!\!\!\!\!-O-CH_2CH_2-$, wherein s is 2 to 4 and t is 1 or 2, $K_{14}^{\oplus}$ is $$-\overset{R_{61}}{\underset{R_{63}}{\oplus N}}-R_{62} \quad , \quad -\overset{R_{64}}{\underset{R_{65}}{\oplus N}}-N\overset{R_{45}}{\underset{R_{46}}{}}\!\!\!\!,$$

$$-\overset{X}{\underset{\phantom{x}}{}}\overset{R_{66}}{\underset{R_{67}}{\overset{H N^{\oplus}}{}}} \quad , \quad \bigcirc\!\!\!\!\!N^{\oplus}-R_{68} \quad \text{or}$$

$$\overset{CH_3}{\underset{\phantom{x}}{\bigcirc}}\!\!\!\!\!N^{\oplus}-R_{68} \quad ,$$

each of $R_{61}$, $R_{62}$, $R_{63}$, $R_{64}$ and $R_{65}$ is independently alkyl or monosubstituted alkyl wherein the substituent of monosubstituted alkyl is hydroxy, cyano or phenyl, each of $R_{45}$ and $R_{46}$ is independently hydrogen or alkyl, or R$_{61}$ and R$_{62}$ taken together and with the nitrogen to which they are joined are pyrrolidinium, piperidinium or morpholinium, or R$_{61}$, R$_{62}$ and R$_{63}$ taken together and with the nitrogen to which they are joined are pyridinium, methylpyridinium, quinolinium or

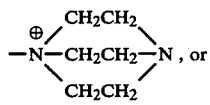

R$_{64}$ and R$_{65}$ taken together and with the nitrogen to which they are joined are pyrrolidinium, piperidinium or morpholinium, or R$_{45}$, R$_{46}$, R$_{64}$ and R$_{65}$ taken together and with the nitrogens to which they are joined are

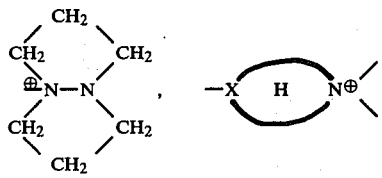

is pyrrolidinium, piperidinium, morpholinium or piperazinium, each of R$_{66}$ and R$_{68}$ is independently alkyl, and R$_{67}$ is alkyl, amino or substituted amino wherein each substituent is independently alkyl, and each alkyl and alkyl chain of each alkylcarbonylamino, alkylcarbonyl, alkylbenzoyl, alkylsulfamoyl, dialkylsulfamoyl, N-alkyl-N-phenylsulfamoyl and monosubstituted alkyl independently has 1 to 4 carbon atoms, and each alkoxy and alkoxy chain of each alkoxycarbonyl independently has 1 to 3 carbon atoms.

8. A compound according to claim 7 having the formula

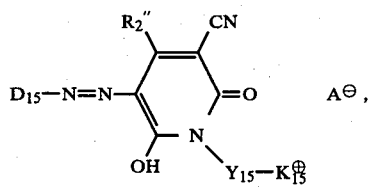

wherein

D$_{15}$ is phenyl, substituted phenyl or naphthyl, wherein substituted phenyl has 1 to 3 substituents and each substituent of substituted phenyl is independently chloro, bromo, nitro, cyano, methyl, methoxy, ethoxy, phenyl, phenoxy, 4-chlorophenoxy, acetamido, benzamido, acetyl, benzoyl, 4-methylbenzoyl, methoxycarbonyl, ethoxycarbonyl, sulfamoyl, N,N-dimethylsulfamoyl, N-ethyl-N-phenylsulfamoyl, phenylsulfamoyl, phenylcarbamoyl, 2,4-dinitroanilino or phenylazo, R$_2''$ is methyl, ethyl or phenyl, Y$_{15}$ is

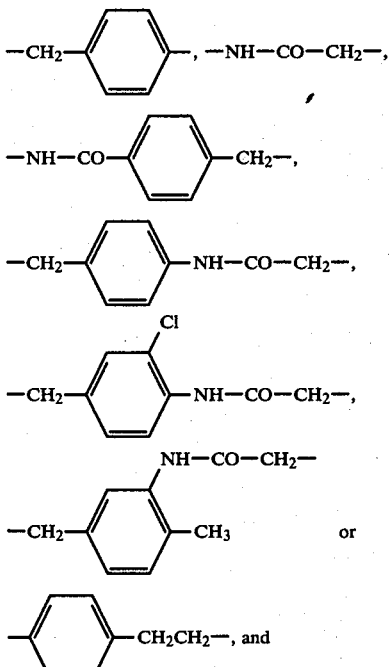

K$_{15}^{\oplus}$ is

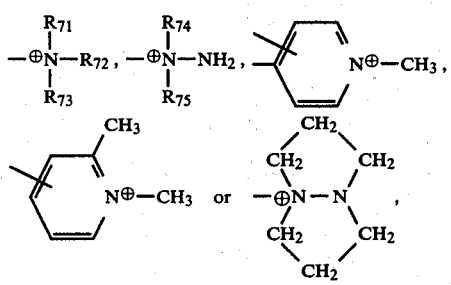

wherein each of R$_{71}$ and R$_{72}$ is independently alkyl of 1 to 4 carbon atoms, 2-hydroxyethyl or 2-cyanoethyl, or R$_{71}$ and R$_{72}$ taken together and with the nitrogen to which they are joined are pyrrolidinium, piperidinium or morpholinium, R$_{73}$ is methyl, ethyl or benzyl, or R$_{71}$, R$_{72}$ and R$_{73}$ taken together and with the nitrogen to which they are joined are pyridinium, 2-methylpyridinium, quinolinium or

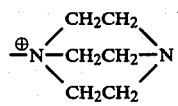

each of R$_{74}$ and R$_{75}$ is independently methyl, ethyl, 2-hydroxyethyl or 2-cyanoethyl, or R$_{74}$ and R$_{75}$ taken together and with the nitrogen to which they are joined are pyrrolidinium, piperidinium or morpholinium, and A$^{\ominus}$ is an anion.

9. A compound according to claim 8 having the formula

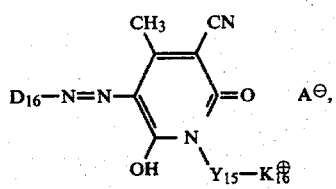

wherein $D_{16}$ is phenyl, 2-methylphenyl, 3-methylphenyl, 4-methylphenyl, 2,5-dimethylphenyl, 2-methoxyphenyl, 4-methoxyphenyl, 4-ethoxyphenyl, 2-chlorophenyl, 3-chlorophenyl, 4-chlorophenyl, 2,5-dichlorophenyl, 3,4-dichlorophenyl, 2,4,6-trichlorophenyl, 2-bromophenyl, 3-bromo-phenyl, 2,4,6-tribromophenyl, 3-chloro-4-methoxyphenyl, 2-methyl-4-chlorophenyl, 3-nitrophenyl, 4-nitrophenyl, 2,4-dinitrophenyl, 2-nitro-4-methylphenyl, 2-methyl-5-nitrophenyl, 2-nitro-4-chlorophenyl, 3-nitro-4-chlorophenyl, 2-chloro-4-nitrophenyl, 2,6-dichloro-4-nitrophenyl, 2-methoxy-4-nitrophenyl, 2-methoxy-5-nitrophenyl, 2-cyano-4-chlorophenyl, 2-biphenylyl, 4-biphenylyl, 3-chloro-6-phenoxyphenyl, 4-(4'-chlorophenoxy)phenyl, 4-acetylphenyl, 2-methoxycarbonylphenyl, 4-ethoxycarbonylphenyl, 4-(4'-methylbenzoyl)-phenyl, 4-phenylcarbamoylphenyl, 2-methoxy-5-sulfamoylphenyl, 4-N,N-dimethylsulfamoylphenyl, 4-phenylsulfamoylphenyl, 2-N-ethyl-N-phenylsulfamoylphenyl, 3-phenylsulfamoyl-4-methylphenyl, 4-acetamidophenyl, 3-benzamidophenyl, 4-benzamidophenyl, 4-phenylazophenyl, 4-(2,4-dinitroanilino)phenyl or naphthyl, $Y_{15}$ is

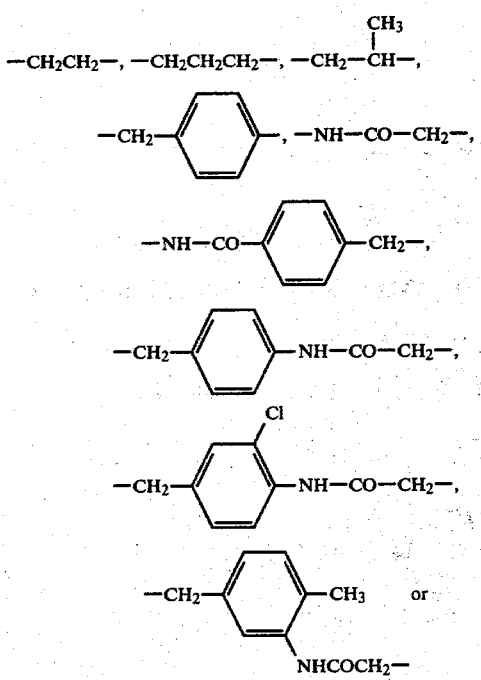

$K_{16}^{\oplus}$ is

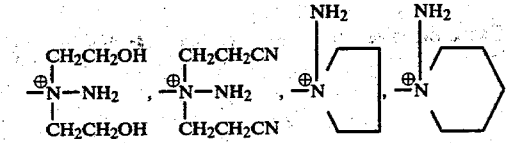

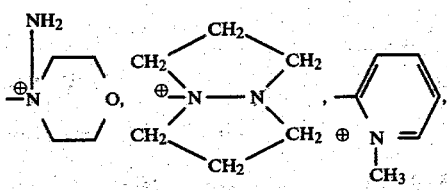

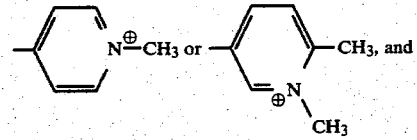

$A^{\ominus}$ is an anion.

10. A compound according to claim 9 wherein $A^{\ominus}$ is chloride or methylsulfate.

11. The compound according to claim 10 having the formula

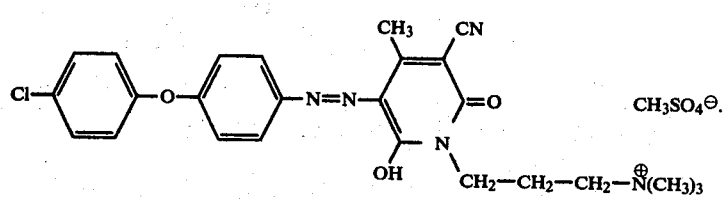

12. The compound according to claim 10 having the formula

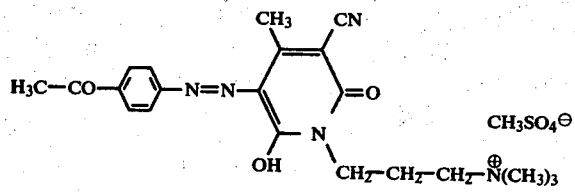

13. The compound according to claim 10 having the formula

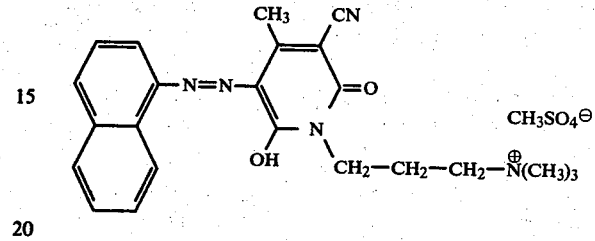

16. The compound according to claim 10 having the formula

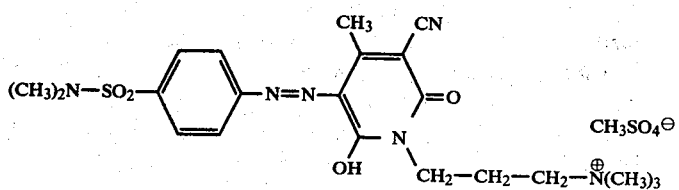

17. The compound according to claim 10 having the formula

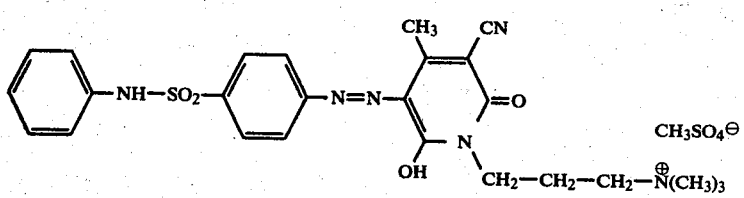

14. The compound according to claim 10 having the formula

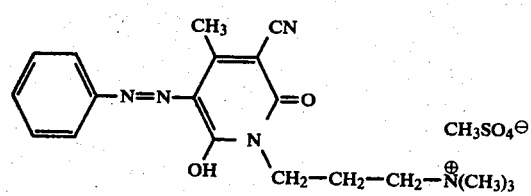

15. The compound according to claim 10 having the formula

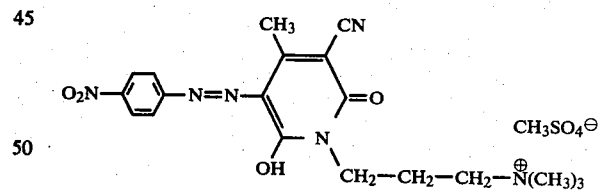

18. A compound according to claim 3 wherein $R_{10}$ is hydrogen.

19. A compound according to claim 4 wherein $R_{10}$ is hydrogen.

20. A compound according to claim 1 having the formula

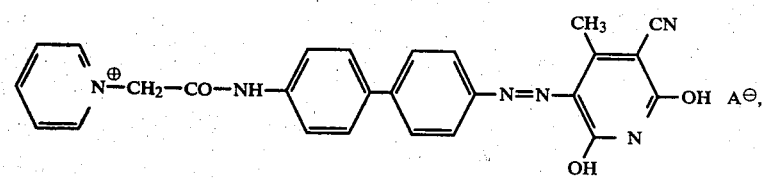

wherein $A^{\ominus}$ is an anion.

21. The compound according to claim 20 wherein $A^\ominus$ is $Cl^\ominus$.

22. A compound according to claim 2 having the formula

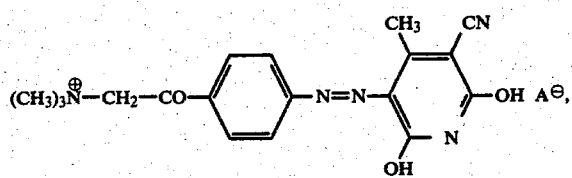

wherein $A^\ominus$ is an anion.

23. The compound according to claim 5 wherein $A^\ominus$ is $CH_3SO_4^\ominus$.

24. A compound according to claim 1 having the formula

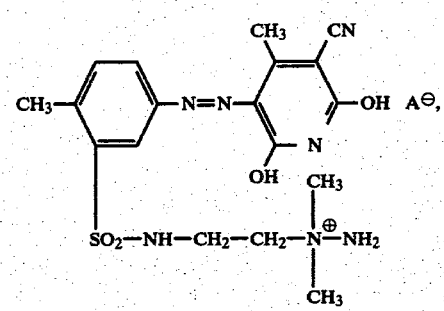

wherein $A^\ominus$ is an anion.

25. The compound according to claim 24 wherein $A^\ominus$ is $Cl^\ominus$.

26. The compound of the formula

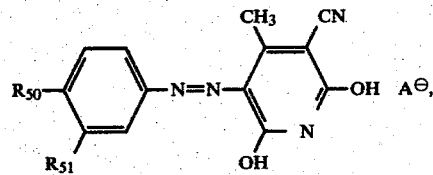

27. A compound according to claim 1 having the formula

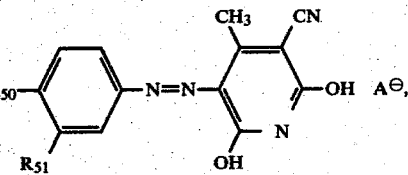

wherein $R_{50}$ is

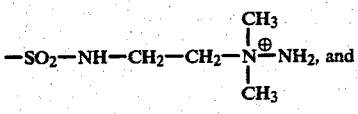

$(CH_3)_3N^\oplus-CH_2-CO-$ or $CH_3-$, $R_{51}$ is hydrogen or $$-SO_2-NH-CH_2-CH_2-\overset{\overset{CH_3}{|}}{\underset{\underset{CH_3}{|}}{N^\oplus}}-NH_2,$$

with the proviso that $R_{51}$ is hydrogen when $R_{50}$ is other than $CH_3-$ and $R_{50}$ is $CH_3-$ when $R_{51}$ is $$-SO_2-NH-CH_2-CH_2-\overset{\overset{CH_3}{|}}{\underset{\underset{CH_3}{|}}{N^\oplus}}-NH_2, \text{ and}$$

$A^\ominus$ is $CH_3SO_4^\oplus$ when $R_{50}$ is $(CH_3)_3N^\ominus-CH_2-CO-$ and is otherwise $Cl^\ominus$.

* * * * *